US009645155B2

United States Patent
Cai et al.

(10) Patent No.: US 9,645,155 B2
(45) Date of Patent: May 9, 2017

(54) METHODS OF SYNTHESIZING γ-AAPEPTIDES, γ-AAPEPTIDE BUILDING BLOCKS, γ-AAPEPTIDE LIBRARIES, AND γ-AAPEPTIDE INHIBITORS OF Aβ$_{40}$ AGGREGATES

(71) Applicants: Jianfeng Cai, Tampa, FL (US); Chuanhai Cao, Temple Terrace, FL (US); Haifan Wu, Tampa, FL (US); Yaqiong Li, Tampa, FL (US); Ge Bai, Tampa, FL (US)

(72) Inventors: Jianfeng Cai, Tampa, FL (US); Chuanhai Cao, Temple Terrace, FL (US); Haifan Wu, Tampa, FL (US); Yaqiong Li, Tampa, FL (US); Ge Bai, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 14/914,960

(22) PCT Filed: Aug. 18, 2014

(86) PCT No.: PCT/US2014/051406
§ 371 (c)(1),
(2) Date: Feb. 26, 2016

(87) PCT Pub. No.: WO2015/031084
PCT Pub. Date: Mar. 5, 2015

(65) Prior Publication Data
US 2016/0209422 A1    Jul. 21, 2016

Related U.S. Application Data

(60) Provisional application No. 61/870,874, filed on Aug. 28, 2013.

(51) Int. Cl.
| | | |
|---|---|---|
| *C40B 50/14* | (2006.01) | |
| *G01N 33/68* | (2006.01) | |
| *A61K 51/04* | (2006.01) | |
| *C07C 271/22* | (2006.01) | |
| *C07K 14/47* | (2006.01) | |
| *B01J 19/00* | (2006.01) | |
| *C07K 5/02* | (2006.01) | |
| *A61K 38/00* | (2006.01) | |

(52) U.S. Cl.
CPC ..... *G01N 33/6845* (2013.01); *A61K 51/0406* (2013.01); *B01J 19/0046* (2013.01); *C07C 271/22* (2013.01); *C07K 5/02* (2013.01); *C07K 14/4711* (2013.01); *G01N 33/6896* (2013.01); *A61K 38/00* (2013.01); *B01J 2219/00592* (2013.01); *B01J 2219/00596* (2013.01); *B01J 2219/00725* (2013.01); *C07C 2103/18* (2013.01); *G01N 2333/4709* (2013.01); *G01N 2500/04* (2013.01); *G01N 2500/20* (2013.01); *G01N 2800/2821* (2013.01)

(58) Field of Classification Search
None
See application file for complete search history.

(56) References Cited

U.S. PATENT DOCUMENTS

| | | |
|---|---|---|
| 5,955,572 A | 9/1999 | Ruoslahti et al. |
| 6,815,426 B2 | 11/2004 | Scialdone et al. |
| 7,795,386 B2 | 9/2010 | Corti et al. |
| 7,928,113 B2 | 4/2011 | Neamati et al. |
| 8,834,840 B1 | 9/2014 | Bull et al. |
| 2009/0148459 A1 | 6/2009 | Woessner et al. |
| 2010/0074844 A1 | 3/2010 | Kolb et al. |

OTHER PUBLICATIONS

Kodadek, T. The rise, fall and reinvention of combinatorial chemistry. Chemical Communications 47, 9757-9763 (2011).
Aquino, C. et al. A biomimetic polyketide-inspired approach to small-molecule ligand discovery. Nature chemistry 4, 99-104 (2012).
Simpson, L.S. & Kodadek, T. A cleavable scaffold strategy for the synthesis of one-bead one-compound cyclic peptoid libraries that can be sequenced by tandem mass spectrometry. Tetrahedron Letters 53, 2341-2344 (2012).
Aditya, A. & Kodadek, T. Incorporation of Heterocycles into the Backbone of Peptoids to Generate Diverse Peptoid-Inspired One Bead One Compound Libraries. Acs Comb Sci 14, 164-169 (2012).
Kodadek, T. Development of antibody surrogates for the treatment of cancers and autoimmune disease. Current opinion in chemical biology 14, 721-727 (2010).
Udugamasooriya, D.G. & Kodadek, T. On-Bead Two-Color (OBTC) Cell Screen for Direct Identification of Highly Selective Cell Surface Receptor Ligands. Current protocols in chemical biology 4, 35-48 (2012).
Zuckermann, R.N. & Kodadek, T. Peptoids as potential therapeutics. Curr Opin Mol Ther 11, 299-307 (2009).
Astle, J.M. et al. Seamless bead to microarray screening: rapid identification of the highest affinity protein ligands from large combinatorial libraries. Chemistry & biology 17, 38-45 (2010).
Kodadek, T. Rethinking screening. Nature chemical biology 6, 162-165 (2010).
Lam, K.S. et al. A New Type of Synthetic Peptide Library for Identifying Ligand-Binding Activity. Nature 354, 82-84 (1991).
Lam, K.S. Editorial: Peptides as cancer therapeutics. Biopolymers 66, 141-141 (2002).
Aina, O.H., Sroka, T.C., Chen, M.L. & Lam, K.S. Therapeutic cancer targeting peptides. Biopolymers 66, 184-199 (2002).

(Continued)

*Primary Examiner* — Christopher M Gross
(74) *Attorney, Agent, or Firm* — Thomas Horstemeyer, LLP

(57) ABSTRACT

Embodiments of the present disclosure provide for γ-AApeptides, γ-AApeptide building blocks, methods of making γ-AApeptides and libraries of γ-AApeptides, methods of screening the γ-AApeptide libraries for desired peptidomimetic activity, and the like. The present disclosure also provides for γ-AApeptides that are inhibitors of Aβ peptide aggregation, methods of inhibiting and disassembling Aβ peptide aggregation, methods of inhibiting the toxicity of Aβ aggregates towards N2a neuroblasotma cells, as well as methods and compounds for treating Alzheimer's disease.

13 Claims, 22 Drawing Sheets

(56) References Cited

OTHER PUBLICATIONS

Copeland, G.T. & Miller, S.J. Selection of enantioselective acyl transfer catalysts from a pooled peptide library through a fluorescence-based activity assay: An approach to kinetic resolution of secondary alcohols of broad structural scope. Journal of the American Chemical Society 123, 6496-6502 (2001).
Kritzer, J.A., Luedtke, N.W., Harker, E.A. & Schepartz, A. A rapid library screen for tailoring beta-peptide structure and function. Journal of the American Chemical Society 127, 14584-14585 (2005).
Hayashi, R. et al. N-acylpolyamine inhibitors of HDM2 and HDMX binding to p. 53. Bioorganic & medicinal chemistry 17, 7884-7893 (2009).
Iera, J.A., Jenkins, L.M.M., Kajiyama, H., Kopp, J.B. & Appella, D.H. Solid-phase synthesis and screening of N-acylated polyamine (NAPA) combinatorial libraries for protein binding. Bioorganic & Medicinal Chemistry Letters 20, 6500-6503 (2010).
Niu, Y. et al. Identification of gamma-AApeptides with potent and broad-spectrum antimicrobial activity. Chemical communications (Cambridge, England) 47, 12197-12199 (2011).
Niu, Y. et al. Cellular Translocation of a gamma-AApeptide Mimetic of Tat Peptide. Molecular pharmaceutics (2012).
Niu, Y., Jones, A.J., Wu, H., Varani, G. & Cai, J. gamma-AApeptides bind to RNA by mimicking RNA-binding proteins. Org Biomol Chem 9, 6604-6609 (2011).
Niu, Y., Hu, Y., Li, X., Chen, J. & Cai, J. [gamma]-AApeptides: design, synthesis and evaluation. New Journal of Chemistry 35, 542-545 (2011).
Wu, H. et al. Solid-Phase Synthesis of gamma-AApeptides Using a Submonomeric Approach. Organic letters 14, 3446-3449 (2012).
Wu, H. et al. Design and synthesis of unprecedented cyclic gamma-AApeptides for antimicrobial development. Chem. Sci. 3 2570-2575 (2012).
Niu, Y. et al. Lipo-gamma-AApeptides as a New Class of Potent and Broad-Spectrum Antimicrobial Agents. Journal of medicinal chemistry 55, 4003-4009 (2012).
Niu, Y. et al. Nanorods Formed from a New Class of Peptidomimetics. Macromolecules, 10.1021/ma3015992 (2012).
Rapireddy, S., He, G., Roy, S., Armitage, B.A. & Ly, D.H. Strand invasion of mixed-sequence B-DNA by acridine-linked, gamma-peptide nucleic acid (gamma-PNA). Journal of the American Chemical Society 129, 15596-15600 (2007).
Yang, Y.A. et al. Radiolabeled gamma-AApeptides: a new class of tracers for positron emission tomography. Chemical Communications 48, 7850-7852 (2012).
Gomez-Martinez, P., Dessolin, M., Guibe, F. & Albericio, F. N-alpha-Alloc temporary protection in solid-phase peptide synthesis. The use of amine-borane complexes as allyl group scavengers. Journal of the Chemical Society-Perkin Transactions 1, 2871-2874 (1999).
Upadhaya, A.R., Lungrin, I., Yamaguchi, H., Fändrich, M. & Thal, D.R. High-molecular weight Aβ-oligomers and protofibrils are the predominant Aβ-species in the native soluble protein fraction of the AD brain. Journal of Cellular and Molecular Medicine, no-no (2011).
Bernstein, S.L. et al. Amyloid beta-protein: monomer structure and early aggregation states of Abeta42 and its Pro19 alloform. Journal of the American Chemical Society 127, 2075-2084 (2005).
Jakob-Roetne, R. & Jacobsen, H. Alzheimer's Disease: From Pathology to Therapeutic Approaches. Angewandte Chemie-International Edition 48, 3030-3059 (2009).
Luo, Y. et al. Abeta42-Binding Peptoids as Amyloid Aggregation Inhibitors and Detection Ligands. ACS Chemical Neuroscience ASAP(2013).
Chafekar, S.M. et al. Branched KLVFF tetramers strongly potentiate inhibition of beta-amyloid aggregation. Chembiochem 8, 1857-1864 (2007).
Cheng, P.N., Spencer, R., Woods, R.J., Glabe, C.G. & Nowick, J.S. Heterodivalent Linked Macrocyclic beta-Sheets with Enhanced Activity against A beta Aggregation: Two Sites Are Better Than One. Journal of the American Chemical Society 134, 14179-14184 (2012).
Cheng, P.N., Liu, C., Zhao, M.L., Eisenberg, D. & Nowick, J.S. Amyloid beta-sheet mimics that antagonize protein aggregation and reduce amyloid toxicity. Nature chemistry 4, 927-933 (2012).
Soto, C. et al. Beta-sheet breaker peptides inhibit fibrillogenesis in a rat brain model of amyloidosis: implications for Alzheimer's therapy. Nature medicine 4, 822-826 (1998).
Zhang G.B. Leibowitz, M.J., Sinko, P.J. & Stein, S. Multiple-peptide conjugates for binding beta-amyloid plaques of Alzheimer's disease. Bioconjugate chemistry 14, 86-92 (2003).
Rahimi, F., Murakami, K., Summers, J.L., Chen, C.H.B. & Bitan, G. RNA Aptamers Generated against Oligomeric A beta 40 Recognize Common Amyloid Aptatopes with Low Specificity but High Sensitivity. PloS one 4(2009).
Ylera, F., Lurz, R., Erdmann, V.A. & Furste, J.P. Selection of RNA aptamers to the Alzheimer's disease amyloid peptide. Biochem Bioph Res Co 290, 1583-1588 (2002).
Pauwels, K. et al. Structural Basis for Increased Toxicity of Pathological A beta(42):A beta(40) Ratios in Alzheimer Disease. Journal of Biological Chemistry 287, 5650-5660 (2012).
Hooper, C.; Killick, R.; Lovestone, S. J Neurochem 2008, 104, 1433.
International Search Report for application PCT/US14/51406, 22 pages, mailed Feb. 4, 2015.

Scheme 1

Scheme 2

Scheme 3

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Chemically synthesized peptide including
      residues 16-20 of the human alpha-beta peptide and capable of
      binding alpha-beta peptide

<400> SEQUENCE: 1

Lys Leu Val Phe Phe
1               5
```

METHODS OF SYNTHESIZING γ-AAPEPTIDES, γ-AAPEPTIDE BUILDING BLOCKS, γ-AAPEPTIDE LIBRARIES, AND γ-AAPEPTIDE INHIBITORS OF Aβ$_{40}$ AGGREGATES

CROSS-REFERENCE TO RELATED APPLICATION

This application is the 35 U.S.C. §371 national stage of, and claims priority to and the benefit of, PCT application PCT/US2014/051406, filed Aug. 18, 2014, which claims priority to and the benefit of U.S. Provisional Application No. 61/870,874, filed on Aug. 28, 2013, herein incorporated by reference in their entirety.

SEQUENCE LISTING

The instant application contains a sequence listing which has been submitted with the instant application. The sequence listing file is named 02065570.txt, is 655 bytes in size, and is incorporated herein by reference in its entirety.

BACKGROUND

One of the most important goals in modern chemical biology and biomedical sciences is to identify molecular ligands that recognize peptides or proteins of interest with high specificity and affinity. These ligands can be used as invaluable biological tools, such as biomarkers for protein purification, detection and targeted imaging, or used as potential drug leads or candidates for therapeutic development. Combinatorial chemistry is a powerful approach for ligand screening, creating a diverse library of compounds, which provides unbiased opportunity for ligand identification when the structural information of targets is not available or not helpful in the rational design technique. In fact, most bioactive molecules are identified through screening efforts. Since peptides have favorable protein binding capabilities and are capable of modular synthesis, early efforts were dedicated to the identification of selective peptide ligands against a variety of targets.

However, natural proteins have drawbacks such as, but not limited to, instability due to susceptibility to proteolysis. Interest in unnatural peptidomimetic ligand libraries developed recently, as these ligands contain unnatural backbones and therefore possess enormous structural diversity and enhanced stability against proteolysis. The examples of peptidomimetic ligands include peptoids, β-peptides, and N-acylated polyamine, etc. However, except for peptoids, applications of such peptidomimetic ligand library are rare. Compared to novel therapeutic and tool ligands, the development of new peptidomimetic ligand libraries lags behind, due in part to the limited availability of backbones and functional diversity, as well as the difficulty in identification of lead compounds. Therefore, peptidomimetic libraries including ligands with novel backbones may facilitate identification of novel molecular probes and drug candidates.

SUMMARY

Embodiments of the present disclosure provide for γ-AApeptides, γ-AApeptide building blocks, methods of making γ-AApeptides and libraries of γ-AApeptides, methods of screening the γ-AApeptide libraries for desired peptidomimetic activity, and the like. The present disclosure also provides for γ-AApeptides that are inhibitors of Aβ peptide aggregation, methods of inhibiting and disassembling Aβ peptide aggregation, methods of inhibiting the toxicity of Aβ aggregates towards N2a neuroblasotma cells, as well as methods and compounds for treating Alzheimer's disease, and the like.

In embodiments, the present disclosure includes γ-AApeptide building blocks having the following structure:

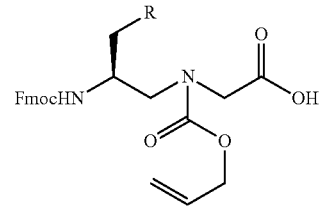

where R is selected from: any amino acid side chain.

The present disclosure also provides methods of making a γ-AApeptide compound, embodiments of such methods including the following steps:

a. providing a first γ-AApeptide building block having the structure of compound X:

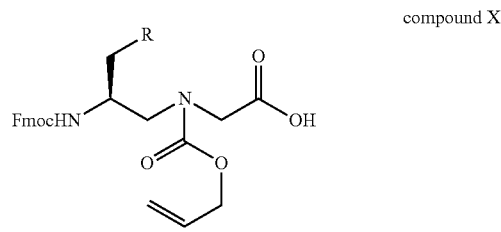

where R is selected from any amino acid side chain;

b. removing the alloc protection group from the γ-AApeptide building block;

c. reacting the compound from step b with an acylating agent including R', where R' is selected from the group consisting of any amino acid side chain,

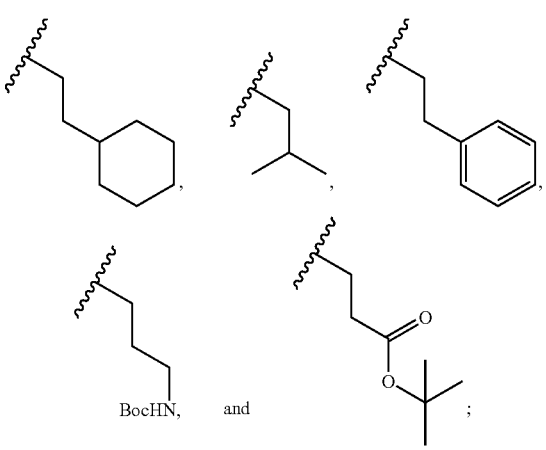

d. reacting the compound from step c with another γ-AApeptide building block having the structure of compound X, where R is independently selected from the R of the first γ-AApeptide building block;

e. optionally repeating steps b to d a desired number of times; and f. removing the protecting groups to obtain the γ-AApeptide compound of Formula I:

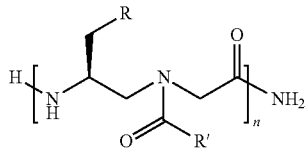

Formula I where n is an integer between 1 and about 20, the bracketed portion of Formula 1 is a repeating unit, except for the identity of R and R', and wherein R and R' are as defined above and are independently selected for each repeating unit.

In embodiment, the present disclosure also includes methods of making a γ-AApeptide library, the method including the following:

a. providing a plurality of synthetic beads functionalized to react with γ-AApeptide building blocks;

b. splitting the beads into a predetermined number of groups and placing each group in a separate reaction vessel;

c. adding a different γ-AApeptide building block to each reaction vessel and reacting the γ-AApeptide building block with the beads, where each γ-AApeptide building block has the structure of compound X

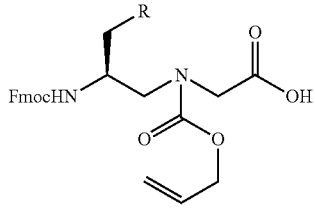

compound X and where the R for the γ-AApeptide building block for each reaction vessel is different from that for every other reaction vessel and is selected from the group consisting of: any amino acid side chain.

d. pooling the bead/γ-AApeptide compounds from each reaction vessel together, splitting the bead/γ-AApeptide compounds into the predetermined number of groups, and placing each group into a separate reaction vessel;

e. removing the alloc protection groups from the bead/γ-AApeptide compounds;

f. adding a different acylating agent to each reaction vessel, where each acylating agent includes an R' group, and where the R' for each different acylating agent is independently selected from the group consisting of: any amino acid side chain,

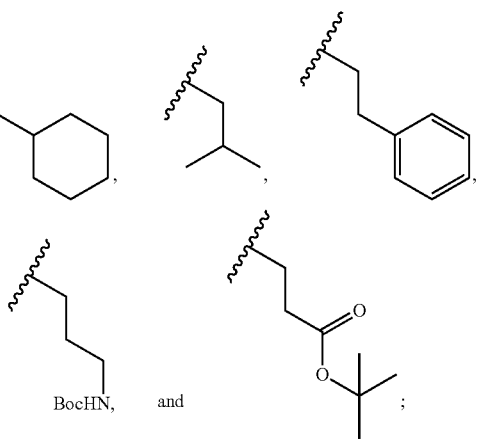

g. pooling the bead/acylated γ-AApeptide compounds from each reaction vessel together, splitting the bead/acylated γ-AApeptide compounds into the predetermined number of groups, and placing each group into the separate reaction vessels;

h. repeating steps c-g n−1 number of times; and i. removing all protecting groups to obtain a library of different γ-AApeptide compounds having a structure of Formula I:

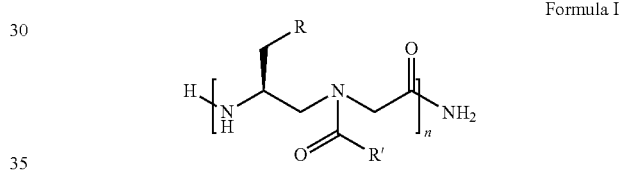

Formula I where for each γ-AApeptide compound, n is an integer between 1 and about 20 and R and R' are as defined above and are independently selected for each repeating unit.

Embodiments of the present disclosure also include methods of screening a library of γ-AApeptides for ligands to a target compound, the method including the following: contacting the γ-AApeptides in the library with a target compound; removing unbound target compound; contacting the library with an antibody capable of binding the target compound; detecting the antibody with a detectable label; and selecting the γ-AApeptide associated with the detectable label, where the selected γ-AApeptide is a ligand capable of binding the target compound.

The present disclosure also includes γ-AApeptides having the following structure:

Compound HW-155-1

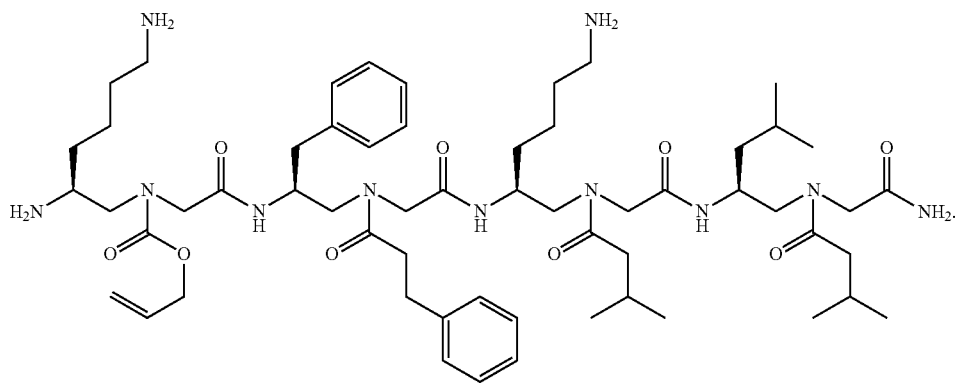

Embodiments of the present disclosure of methods of inhibiting aggregation of Aβ peptides include exposing Aβ peptides to a compound comprising γ-AApeptide HW-155-1.

The present disclosure also includes methods of detecting Aβ peptides, the method including the following: contacting a sample with a compound including γ-AApeptide HW-155-1 coupled to a detectable label, and screening the sample for the detectable label, where detection of the detectable label indicates the presence of an Aβ peptide.

Embodiments of methods of disrupting Aβ peptide aggregates, Aβ peptide fibrils, or both, of the present disclosure include: contacting the aggregates, fibrils or combination thereof with a composition including γ-AApeptide HW-155-1.

The present disclosure includes methods of inhibiting aggregation of Aβ peptides, disrupting Aβ peptide aggregates, disrupting Aβ peptide fibrils, or a combination thereof in a patient with Alzheimer's disease, embodiments of the method including: administering to the patient a pharmaceutical composition including γ-AApeptide HW-155-1.

Embodiments of methods of treating Alzheimer's disease according to the present disclosure include administering to a patient in need thereof a therapeutically effective amount of a composition including γ-AApeptide HW-155-1.

In embodiments, the present disclosure includes methods of inhibiting the death of N2a neuroblasotma cells. Embodiments of such methods include contacting N2a neuroblasotma cells with a composition including γ-AApeptide HW-155-1, such that death of the N2a neuroblasotma cells is reduced compared to death of N2a neuroblastoma cells in the absence of γ-AApeptide HW-155-1.

Other methods, compositions, features, and advantages of the present disclosure will be or become apparent to one with skill in the art upon examination of the following drawings and detailed description. It is intended that all such additional compositions, methods, features, and advantages be included within this description, and be within the scope of the present disclosure.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 14C is a bar graph showing the ratio of aggregation after 24 h. Aggregation control (100%) is set as the change of fluorescence of 2.5 μM $A\beta_{40}$ in Tris (pH 7.5) buffer. The concentration of ThT is 5 μM. Excitation: 440 nm; emission: 482 nm.

DETAILED DESCRIPTION

Figure 1:
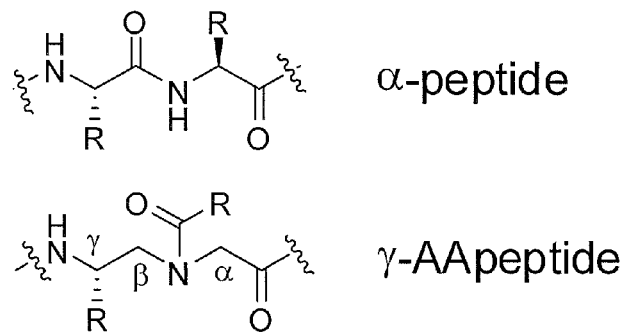
FIG. 1 illustrates the chemical structure of an α-peptide and a γ-AApeptide.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Any publications and patents cited in this specification that are incorporated by reference are incorporated by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of organic chemistry, biochemistry, molecular biology, medicine, pharmacology, imaging, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a cell" includes a plurality of cells. In this specification and in the embodiments that follow, reference will be made to a number of terms that shall be defined to have the following meanings unless a contrary intention is apparent.

Prior to describing the various embodiments, the following definitions are provided and should be used unless otherwise indicated.

DEFINITIONS

In describing the disclosed subject matter, the following terminology will be used in accordance with the definitions set forth below.

The terms "polypeptides" and "peptides" include proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of this disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073, (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence, or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also include non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethyl homocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system including an *E. coli* S30 extract and commercially available enzymes and other reagents. Proteins are purified by chromatography. (Robertson, et al., J. Am. Chem. Soc., 113: 2722, 1991; Ellman, et al., Methods Enzymol., 202: 301, 1991; Chung, et al., Science, 259: 806-9, 1993; and Chung, et al., Proc. Natl. Acad. Sci. USA, 90: 10145-9, 1993). In a second method, translation is carried out in *Xenopus* oocytes by microinjection of mutated mRNA and chemically aminoacylated suppressor tRNAs (Turcatti, et al., J. Biol. Chem., 271: 19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., Biochem., 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., Protein Sci., 2: 395-403, 1993).

As used herein, the term "peptidomimetics" refers to compounds having a protein-like chain that are designed to mimic peptides, but that have an altered chemistry that does not occur naturally, such as an altered backbone or the incorporation of non-natural amino acids.

The term "γ-AApeptide" refers herein to a class of peptidomimetic compounds having the backbone structure shown below (compared to a natural α peptide).

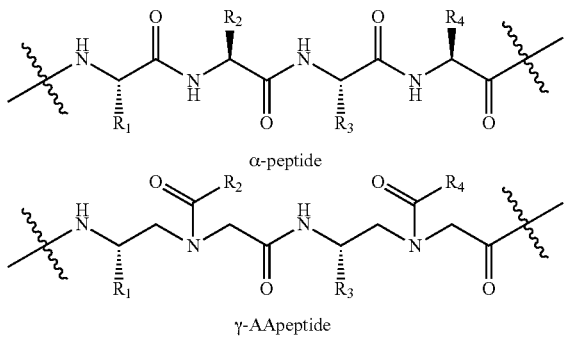

α-peptide

γ-AApeptide

The repeating unit of the γ-AApeptide backbone (the "γ-AApeptide subunit"), as compared to two adjacent amino acid residues of an α-peptide, contains two side chains (including the R groups), one of which is an α-amino acid side chain, while the other comes from a carboxylic acid residue on the tertiary amide nitrogen. The term "γ-AApeptide compound" refers to compounds of the present disclosure having the γ-AApeptide backbone structure shown above, and can include a single γ-AApeptide as well as an oligomeric or polymeric γ-AApeptide. For instance, embodiments of γ-AApeptide compounds of the present disclosure include compounds having the structure of Formula 1, below. As used herein, the term "γ-AApeptide building block" refers to a compound used in the preparation of a γ-AApeptide compound, such as an γ-AApeptide polymer. The γ-AApeptide building block can have a protecting group, such as an alloc protecting group (—$CO_2C_3H_5$) the γ-AApeptide building block will become a γ-AApeptide subunit within a longer-chain γ-AApeptide compound.

As used herein, the term "detectable label", "imaging agent", or "imaging compound" refers to labeled compounds that are capable of serving as imaging agents and that are capable of producing a detectable signal.

By "administration" is meant introducing a compound of the present disclosure into a subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used.

In accordance with the present disclosure, "a detectably effective amount" of the imaging agent of the present disclosure is defined as an amount sufficient to yield an acceptable image using equipment that is available for clinical use. A detectably effective amount of the imaging agent of the present disclosure may be administered in more than one injection. The detectably effective amount of the imaging agent of the present disclosure can vary according to factors such as the degree of susceptibility of the individual, the age, sex, and weight of the individual, idiosyncratic responses of the individual, the dosimetry, and the like. Detectably effective amounts of the imaging agent of the present disclosure can also vary according to instrument and film-related factors. Optimization of such factors is well within the level of skill in the art.

As used herein "inhibit" or "inhibiting" an activity indicates that something (e.g., ligand, antigen, antagonist, etc.) acts to reduce or prevent (completely or partially) the target activity (e.g., protein aggregation, formation of aggregates and/or fibrils, etc.), thereby reducing or preventing the occurrence of an activity or a result, as compared to the amount of that activity or result in the absence of the inhibiting factor (the "inhibitor").

The term "therapeutically effective amount" as used herein refers to that amount of the compound being administered which will relieve to some extent one or more of the symptoms of a disease, a condition, or a disorder being treated.

"Treating" or "treatment" of a disease (or a condition or a disorder) includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). These terms also mean that the life expectancy of an individual affected with a terminal illness will be increased or that one or more of the symptoms of the disease will be reduced.

As used herein, the term "host" or "organism" includes humans, mammals (e.g., cats, dogs, horses, etc.), poultry, living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a host. The term "living host" refers to host or organisms noted above that are alive and are not dead. The term "living host" refers to the entire host or organism and not just a part excised (e.g., a liver or other organ) from the living host.

The term "sample" can refer to a tissue sample, cell sample, a fluid sample, and the like. The sample may be taken from a host. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue. In the present disclosure, the source of the sample is not critical.

The term "detectable" refers to the ability to detect a signal over a background signal.

The term "detectable signal" is a signal derived from non-invasive imaging techniques such as, but not limited to, fluorescent imaging, positron emission tomography (PET), single photon emission computed tomography (SPECT), optical imaging, magnetic resonance imaging (MRI), computer topography (CT), or ultrasound. The detectable signal is detectable and distinguishable from other background signals that may be generated from the host or sample. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between detectable signal and the background. Standards and/or calibration curves can be used to determine the relative intensity of the detectable signal and/or the background.

As used herein, the term "amino acid side chain" refers to the side chain moiety of an amino acid that does not form part of the backbone of a peptide chain (see, e.g., Table 1). The side chain is the portion of the amino acid that provides the identity of the amino acid by differentiating it from other amino acids, which all have the basic amino and carboxylic acid functional groups.

General Discussion:

The present disclosure provides novel peptidomimetics, including γ-AApeptides, γ-AApeptide building blocks and methods of making the γ-AApeptides with various functional groups and libraries of γ-AApeptides. The present disclosure also includes methods of screening the γ-AApeptide libraries for γ-AApeptides with specific and/or desired peptidomimetic activity. The present disclosure further provides novel γ-AApeptides that are inhibitors of Aβ peptide aggregation, both preventing and disassembling Aβ peptide aggregation and inhibiting the toxicity of Aβ aggregates towards N2a neuroblasotma cells, as well as methods and compounds for treating Alzheimer's disease.

As described above, it would be desirable to have peptidomimetic ligands of various functions that are stable and resistant to proteolytic degradation. Also, there is a need for the further development of peptidomimetics that can recognize and bind various receptors with increased stability, affinity, and specificity in both in vitro and in vivo, to facilitate the development of novel therapeutics and diagnostics. Described herein are embodiments of γ-AApeptides, γ-AApeptide building blocks, γ-AApeptide libraries, and methods of making the γ-AApeptides and libraries as well as methods of screening the libraries for γ-AApeptides with specific activities. The present disclosure also describes a specific γ-AApeptide compound with activity related to Aβ protein aggregation. In the following disclosure, various specific embodiments are described. It is to be understood that those embodiments are example implementations of the disclosed inventions and that alternative embodiments are possible. All such embodiments are intended to fall within the scope of this disclosure.

The development of novel non-natural ligand libraries will enable identification of highly selective receptor ligands, molecular probes, and drug candidates. Peptidomimetics are ideal ligands as they not only retain favorable peptide-like characteristics such as high protein-binding specificity, but also possess unique advantages including enormous diversity and enhanced stability against proteolysis. However, the reports of new peptidomimetic ligand libraries are rare, due in part to the limited availability of peptidomimetic classes. The present disclosure provides methods for the design, synthesis, characterization and evaluation of an unprecedented class of peptidomimetic ligand library, a γ-AApeptide library.

As described in the examples below, this new synthetic approach was developed by introducing a new γ-AApeptide building block, from which γ-AApeptides with virtually any functional groups can be synthesized with high efficiency and ease. A novel class of γ-AApeptide "one-bead-one-compound" (OBOC) library was prepared using the split-and-pool method. This 192,000-member γ-AApeptide library was demonstrated to be a valuable source of novel protein/peptide ligands. In addition, a hit was identified: a small γ-AApeptide HW-155-1 that can effectively prevent and disassemble Aβ$_{40}$ aggregation. This γ-AApeptide has also been shown to remove the toxicity of Aβ$_{42}$ aggregates towards N2a neuroblastoma cells. As such, this is not only the first report of the development of γ-AApeptide combinatorial library; in addition, HW-1551-1 is also one of the most potent small molecule inhibitors of Aβ aggregation. The results presented in the examples below suggest that γ-AApeptides are ideal candidates for the identification and development of novel ligands and drug candidates.

γ-AApeptides

The compounds of the present disclosure represent a new class of oligomeric peptidomimetics, termed "γ-AApeptides", which was developed to advance the application of peptidomimetics in chemical biology and biomedical sciences. The γ-AApeptides of the present disclosure have the basic backbone structure shown below alongside the structure of the naturally occurring α-peptides, also depicted in FIG. 1.

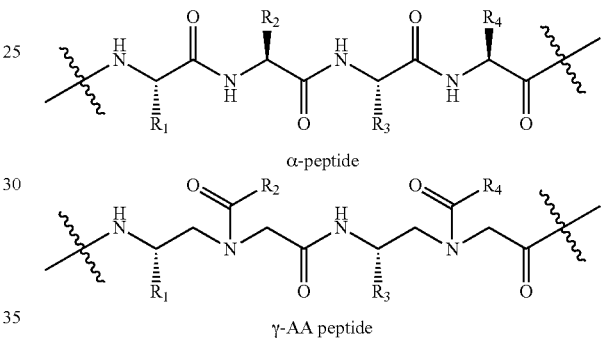

Compared to natural α-peptides, the repeating unit of the γ-AApeptide backbone contains two side chains, one of which is an α-amino acid side chain, while the other comes from a carboxylic acid residue on the tertiary amide nitrogen. As such, γ-AApeptides can project an identical number of side functional groups as conventional peptides of the same length. Such γ-AApeptides are designed so that they can be efficiently synthesized and easily derivatized, while potentially keeping the structural and functional properties of conventional peptides. Since half of side chains can come from any carboxylic acids, there is great potential for generating chemically diverse γ-AApeptide libraries. γ-AApeptides can project virtually any functional groups through acylation, and they can contain the same number of functional groups as peptides of same lengths. Additional details regarding the γ-AApeptides of the present disclosure and methods of making and using the compounds of the present disclosure can be found in the Examples below.

Due to the presence of N-acylated-N-aminoethyl amino acid units (FIG. 1) derived from γ-PNAs, these compounds were termed "γ-AApeptides". Each unit (building block) of the γ-AApeptide is comparable to a dipeptide residue in a canonical peptide. As such, γ-AApeptides essentially project an identical number of functional groups as conventional peptides of the same length. Half of the side chains of γ-AApeptides are chiral, which may impose conformational bias to the molecular ligands similar to conventional peptides, and presumably lead to the ligands with improved specificity and affinity. Since other side chains are introduced through acylation of the nitrogen on the backbone by carboxylic acids or acyl chlorides, there a wide potential exists for generating γ-AApeptide libraries with chemically diverse functional groups.

Moreover, γ-AApeptides are highly resistant to proteolytic degradation, making them ideal candidates to be molecular probes or therapeutic candidates. Indeed, certain γ-AApeptides can recognize HIV-1 RNA with high affinity, translocate across mammalian cell membranes, modulate p53/MDM2 protein-protein interactions, and specifically disrupt bacterial membranes by mimicking the mechanism of natural antimicrobial peptides. In addition, γ-AApeptides can also self-assemble into novel nanostructures. These findings demonstrate the enormous potential of γ-AApeptides for their applications in chemical biology, material science and biomedical sciences.

However, to further expand the biological potential of γ-AApeptides, such as combinatorial development, it would be beneficial to develop a simple and flexible synthetic approach for generating γ-AApeptides. γ-AApeptides were previously synthesized on solid phase using Fmoc γ-AApeptide building blocks (as described in Niu, Y. et al., *New Journal of Chemistry* 35, 542-545 (2011), hereby incorporated by reference herein), which may not be ideal for combinatorial ligand discovery. For instance, to synthesize a di-block γ-AApeptide (comparable to a tetrapeptide in length) library, with the availability of 10 Fmoc-amino aldehydes and 10 carboxylic acids, 100 building blocks have to be prepared. Although a submonomeric approach was developed for the synthesis of γ-AApeptides that circumvents the necessity of preparing γ-AApeptide building blocks (Wu, H. et al., *Organic Letters* 14, 3446-2449 (2012), hereby incorporated by reference herein), the synthetic procedure is tedious and it does not consistently produce crude products with constant high purity. High purity is a factor to be considered in the preparation of one-bead-one-compound (OBOC) ligand libraries. Thus the present disclosure describes the development of a new method of synthesis for γ-AApeptides and new γ-AApeptide building blocks for use in the synthetic methods of the present disclosure.

The γ-AApeptide building blocks of the present disclosure, having the structure of compound X below, can be used in the synthesis of γ-AApeptides of the present disclosure having the structure of Formula I.

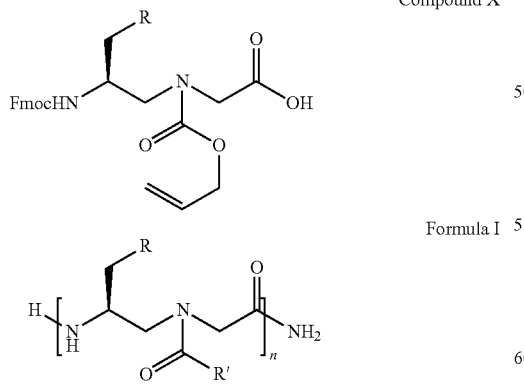

R in compound X and formula 1 can include groups such as, but not limited to, any amino acid side chain. For instance, in embodiments, R can be, but is not necessarily limited to, one of the amino acid side chains in Table 1 below:

TABLE 1

| Amino Acid Side Chain Moeity | Amino Acid |
| --- | --- |
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_3^+$ | Lysine |
| —(CH$_2$)$_3$NHC(NH$_2$)NH$_2^+$ | Arginine |
| —CH$_2$-imidazole | Histidine |
| —CH$_2$COO— | Aspartic Acid |
| —CH$_2$CH$_2$COO— | Glutamic Acid |
| —CH$_2$CONH$_2$ | Asparagine |
| —CH$_2$CH$_2$CONH$_2$ | Glutamine |
| —CH$_2$-phenyl | Phenylalanine |
| —CH$_2$-C$_6$H$_4$-OH | Tyrosine |
| —CH$_2$-indole | Tryptophan |
| —CH$_2$SH | Cysteine |
| —CH$_2$CH$_2$SCH$_3$ | Methionine |
| —CH$_2$OH | Serine |
| —CH(OH)CH$_3$ | Threonine |

R' in Formula I can be any functional group, and in embodiments includes, but is not limited to, any amino acid side chain or any of the following functional groups:

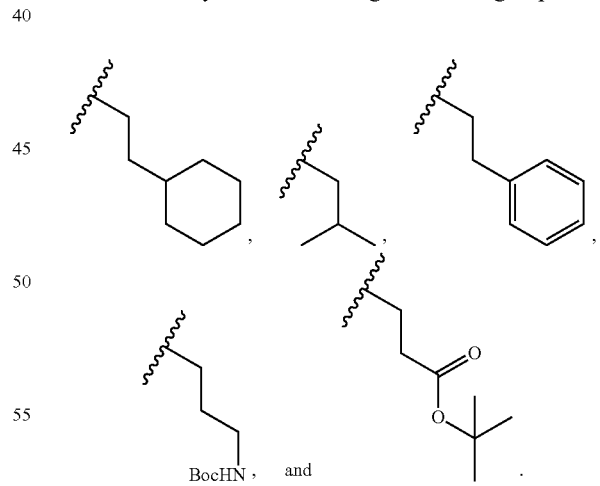

Additionally, it will be understood that Formula I can be extended so that the γ-AApeptide backbone continues (e.g., n can be any integer, such as, but not limited to 1-10, 1-20, 1-50, and so on, including any intervening ranges). It will also be understood that that the R and R' groups can be different for each repeating unit (e.g., the unit in brackets in Formula I), such that each γ-AApeptide subunit can have a different value of R and R' than every other subunit with a single compound of Formula I. Thus, for each subunit, R and R' are independently selected from the group of compound listed herein.

The building block with the structure of compound X is an N-alloc protected γ-AApeptide. Use of this building block in the methods of synthesis of the present disclosure, described below allows the flexibility to add γ-AApeptide subunits with a wide variety of side groups, enabling the creation of large, diverse libraries of γ-AApeptides of various lengths. Methods of synthesis according to the present disclosure will be described in greater detail below.

Methods of Synthesizing

Embodiments of the present disclosure also include methods of synthesizing the γ-AApeptide compounds of the present disclosure having Formula I, above, where n can essentially be any integer, since the γ-AApeptides can be synthesized to any length. In embodiments, n is between 1 and about 20. Each repeating subunit can have different values for R and R' from each other subunit, though with the great number of possible combinations, it is also possible that in a single chain γ-AApeptide, the value for R and/or R' for one or more subunits may be the same as well. However, the flexibility of the synthesis methods of the present disclosure, allow any number of combinations, such as illustrated by the embodiment described in the examples.

Briefly, methods of synthesizing γ-AApeptide compounds of the present disclosure include providing a first N-alloc protected γ-AApeptide building block having the structure of compound X, above. In embodiments, the first γ-AApeptide building block is coupled to a solid support, such as a synthetic bead (e.g., TentaGel NH$_2$ resin beads, Rink amide resin, and the like). Then, the first γ-AApeptide building block is deprotected (e.g., by removal of the alloc protecting group). Then the unprotected nitrogen on the γ-AApeptide backbone is acylated by reaction with an acylating agent. In embodiments the acylating agent is any of a variety of carboxylic acids or acyl chlorides. The acylating agent includes an R' group for the γ-AApeptide subunit and is thus selected according to the desired functional group. The acylating agent can be a carboxylic acid or acyl chloride with a side chain selected from any amino acid side chain or one of the other functional groups listed above for R'.

In embodiments, the carboxylic acids and acyl chlorides can be, but are not limited to, the following:

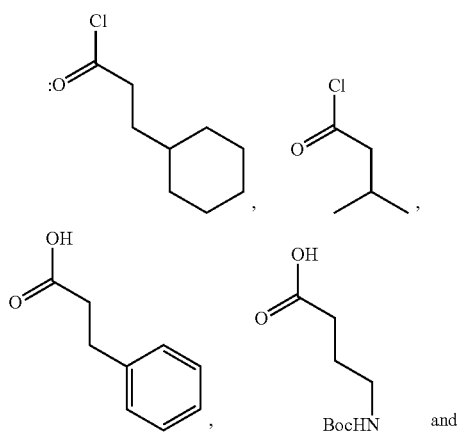

-continued

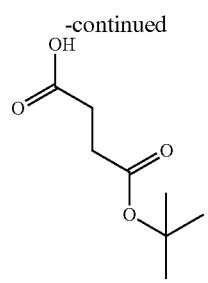

Then, the acylated γ-AApeptide compound is reacted with a second alloc protected γ-AApeptide building block having the structure of compound X, where the R of this subsequent γ-AApeptide building block is independently selected from the R of the previous γ-AApeptide subunit (e.g., the R group of the subsequence alloc protected γ-AApeptide can be the same or different than the R group of the first γ-AApeptide unit).

Then the process is optionally repeated: the subunit is de-protected and reacted with another acylating agent, which may be the same or different from the acylating agent used for the previous γ-AApeptide subunit (e.g., the identity of the core of the acylating agent as well as the R' group on the acylating agent is independently selected from R' of the previous γ-AApeptide subunit). The process is repeated a desired number of times, adding subsequent γ-AApeptide building blocks and then acylating to add R' functional groups, until the desired length of γ-AApeptide compound is obtained. Due to the flexibility of this method and the use of basic building blocks, vast libraries of γ-AApeptides can be synthesized using this procedure, as described below.

γ-AApeptide Libraries

In embodiments, the methods of synthesis of the present disclosure are modified and used in a split and pool method to create large, diverse libraries of γ-AApeptide compounds. In the methods of the present disclosure for making a γ-AApeptide library, a plurality of synthetic beads is functionalized to react with the γ-AApeptide building blocks of the present disclosure. In embodiments, the solid phase (e.g., beads) is functionalized, such as by reaction with an Fmoc protected peptide subunit, such as, but not limited to Fmoc-Met-OH. The Fmoc group is then removed to leave an amine group for reaction with the γ-AApeptide building blocks.

Then the beads are split into separate vessels (e.g. a large number of beads are divided into groups and each group is placed in a separate vessel). Then a different γ-AApeptide building block of compound X (e.g., the building block of compound X for each vessel has a different R group) is placed into each vessel (e.g., one type of γ-AApeptide building block per vessel) to react with the beads. Then the beads (with the first γ-AApeptide subunit now attached) are pooled together and then split again into groups and placed back in the reaction vessels (such that now the beads in each reaction vessel have various first γ-AApeptide subunits). Then the alloc protection groups are removed from the γ-AApeptide backbone and a different acylating agent is added to each reaction vessel (e.g., one type of acylating agent per vessel). Each type of acylating agent can have a different R' group and, in embodiments, each may be a carboxylic acid or acyl chloride. After acylation, the beads (containing the growing γ-AApeptide compound) are again pooled and split back into the reaction vessels. A subsequent γ-AApeptide building block is then added to each vessel, where again the type γ-AApeptide building block is different for each vessel. This splitting/pooling process is continued until the desired length of γ-AApeptide compound is achieved. For a γ-AApeptide of Formula I, with n number of repeating units, after the first repeating unit is formed, the process is repeated n−1 number of times in order to obtain a γ-AApeptide chain with n number of repeating units. At that point all beads with their attached γ-AApeptide compounds are pooled together, providing a diverse library of different γ-AApeptides. Optionally, the remaining protecting groups can be removed.

The present disclosure thus includes libraries of γ-AApeptide compounds of various lengths and compositions having unlimited side groups and combinations of side groups. Embodiments of the present disclosure also include methods of screening the γ-AApeptide libraries for γ-AApeptide compounds with specific activities, such as but not limited to, an affinity for a selected target, ligand binding activity, inhibiting activity toward a specific target or activity, therapeutic activity, and the like.

ligands and/or Aβ peptide aggregate inhibitors may be beneficial in modulation of Aβ peptide aggregation, detection of Aβ peptides and Aβ peptide aggregates, inhibition of Aβ aggregate formation, disruption of Aβ peptide aggregates and fibrils, and in therapeutic compositions and methods for the treatment of Alzheimer's disease or other conditions associated with Aβ peptide aggregate toxicity towards N2a neuroblastoma cells.

As described in the examples below, a γ-AApeptide library was screened and a γ-AApeptide was identified that is capable of binding Aβ peptides, including $A\beta_{40}$ and $A\beta_{42}$. As reported in the example this Aβ peptide was also shown to inhibit Aβ aggregation, prevent formation of Aβ aggregates and disrupt already existing Aβ aggregates and fibrils, and reverse the toxicity of Aβ peptides to N2a neuroblastoma cells.

Thus, embodiments of the present disclosure also include γ-AApeptide HW-155-1 having the following structure:

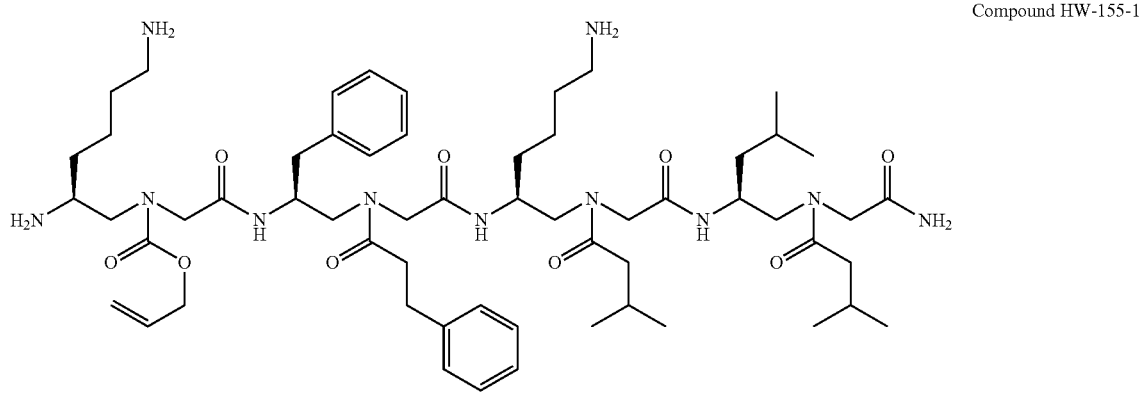 [SMILES: C=CCOC(=O)N(CC(=O)N[C@@H](Cc1ccccc1)CN(CC(=O)N[C@@H](CCCCN)CN(CC(=O)N[C@@H](CC(C)C)CN(CC(N)=O)C(=O)CC(C)C)C(=O)CC(C)C)C(=O)CCc1ccccc1)C[C@@H](N)CCCCN]

Compound HW-155-1

In embodiments the libraries can be screened for ligands to a specific target by contacting the libraries with a specific target compound. Then various methods can be used to detect binding between the target compound and one or more γ-AApeptides from the library. In embodiments, a sandwich-type assay can be used to detect binding. After contacting the library with the target compound, unbound target compound is removed (e.g., by washing the beads). Then an anti-target compound antibody (e.g., an antibody capable of binding the target compound) is added to the library to bind to any bound target compound. Then a second antibody can be used to bind to the first antibody, where the second antibody has a detectable label capable of producing a detectable signal. It will be understood that other methods of detection known to those of skill in the art can also be employed within the scope of the present disclosure.

γ-AApeptide Inhibitors of Aβ Aggregation

Embodiments of the present disclosure include screening a γ-AApeptide library for ligands of Aβ peptides and/or modulators of Aβ peptide aggregation. In embodiments, Aβ peptides include, but are not limited to, $A\beta_{40}$ and $A\beta_{42}$. In embodiments, modulators of Aβ peptide aggregation may inhibit (including reducing and/or prevention of) Aβ aggregation and may further inhibit and/or disrupt the existing Aβ aggregates and/or Aβ fibrils formed Aβ peptide aggregates. Such aggregates and fibrils can be toxic to N2a neuroblasotma cells and are implicated in associated disorders, such as Alzheimer's disease. Thus, identification of Aβ peptide The present disclosure also includes compositions including compound HW-155-1, pharmaceutical compositions including HW-155-1 and a pharmaceutically acceptable carrier.

The present disclosure further includes methods for using γ-AApeptide HW-155-1. In embodiments, γ-AApeptide HW-155-1 can be used in methods of inhibiting aggregation of Aβ peptides by exposing Aβ peptides to a compound including γ-AApeptide HW-155-1, where Aβ aggregation in the presence of HW-155-1 is reduced as compared to Aβ peptides in the absence of HW-155-1. Other methods of the present disclosure include inhibiting the formation of Aβ fibrils or disrupting formed Aβ peptide aggregates, Aβ peptide fibrils, or both by contacting the aggregates, fibrils, or combination with a composition including compound HW-155-1, such that the presence of and/or formation of Aβ peptide aggregates, Aβ peptide fibrils, or both are reduced in the presence of HW-155-1 as compared to in the absence of HW-155-1. The above methods of inhibiting aggregation, disrupting aggregates, fibrils, etc., and detecting Aβ peptides and peptide aggregates, fibrils, etc. can be performed in vivo or in vitro. Embodiments of the present disclosure also include methods of treating Alzheimer's disease or other disorders involving the loss of N2a neuroblastoma cells associated with Aβ peptide fibrils and/or aggregates by administering a therapeutically effective amount of a composition including compound HW-155-1 to a patient in need of treatment. Methods of the present disclosure also include methods of inhibiting the death of N2a neuroblastoma cells by contacting the N2a neuroblastoma cells with a composition comprising γ-AApeptide HW-155-1, such that the γ-AApeptide HW-155 inhibits formation of Aβ peptide fibrils so that the death of the N2a neublasotma cells is reduced compared to death of N2a neuroblastoma cells in the absence of γ-AApeptide HW-155-1.

The present disclosure also includes methods of detecting Aβ peptides by contacting a sample with a compound including γ-AApeptide HW-155-1 coupled to a detectable label and screening the sample for the detectable label, wherein detection of the detectable label indicates the presence of an Aβ peptide. Embodiments of such methods can also include removing unbound γ-AApeptide HW-155-1 coupled to a detectable label and other detection steps known to those of skill in the art.

Embodiments of the present disclosure also include pharmaceutical compositions including the γ-AApeptides of the present disclosure (e.g., γ-AApeptide HW-155-1), as salt, solvate or hydrate thereof, and a pharmaceutically acceptable carrier. The present disclosure also provides labeled γ-AApeptides, where the γ-AApeptides are coupled to a detectable label. The present disclosure also includes pharmaceutical compositions including a detectably effective amount of labeled γ-AApeptides of the present disclosure, where the label is capable of being detected by observation or an imaging device, such as a positron emission technology imaging apparatus (e.g., a PET scanner). In embodiments, the label is a fluorescent label or radiolabel capable of detection by a PET scanning device.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Introduction

The present example reports the development of a new synthetic approach to synthesize γ-AApeptides containing virtually any functional groups at high efficiency with ease. To demonstrate the feasibility of γ-AApeptides for ligand library development using the new approach, a novel class of γ-AApeptide OBOC library was prepared via split-and-pool methods. From this 192,000-member γ-AApeptide library, using high resolution tandem mass spectrometry and de novo sequencing, a small γ-AApeptide was identified to strongly prevent and reverse $A\beta_{40}$ aggregation. This γ-AApeptide is also capable of rescuing N2a neuroblastoma cells by removing the toxicity of Aβ aggregates. It is also one of the most potent small molecules shown to disrupt this pathologically-relevant process. These results suggest that the γ-AApeptide library is a useful source of novel peptide/protein ligands, which are ideal candidates for the identification and development of novel molecular probes and drug candidates.

Results and Discussion

Figure 2:
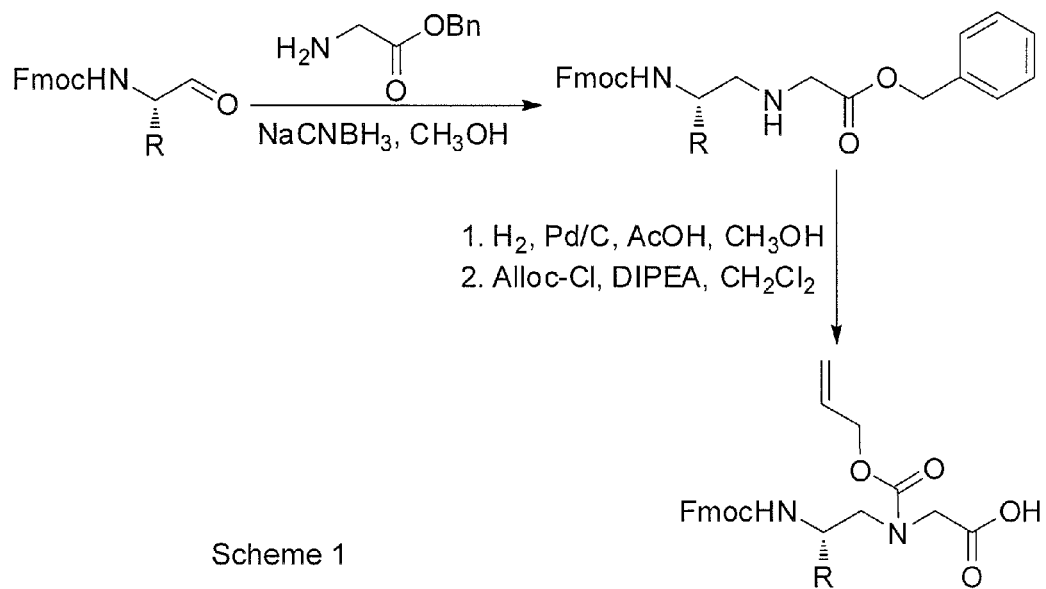
FIG. 2 illustrates scheme 1 showing an embodiment of the present disclosure for synthesis of N-alloc protected γ-AApeptide building blocks.
Figure 3:
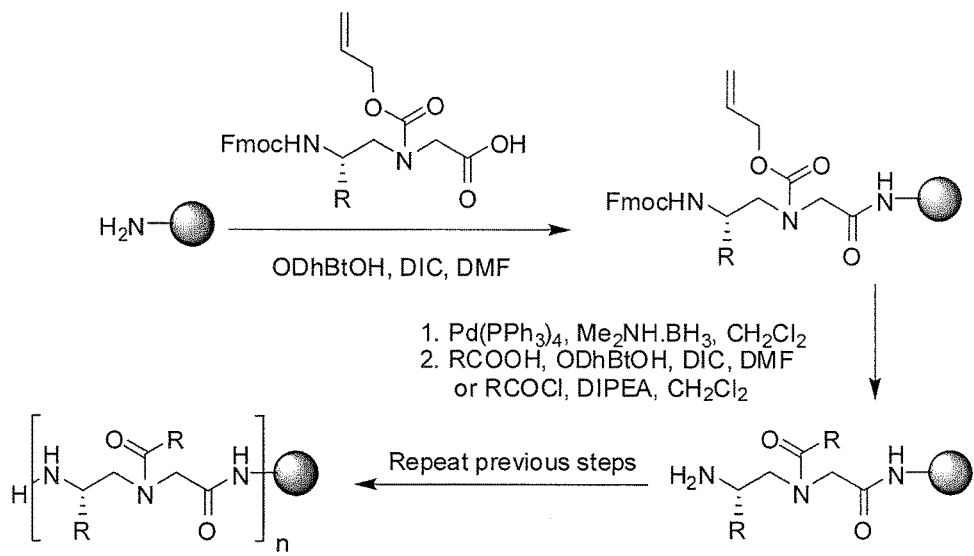
FIG. 3 illustrates scheme 2 showing an embodiment of the present disclosure for synthesis of γ-AApeptides.
Figure 4:
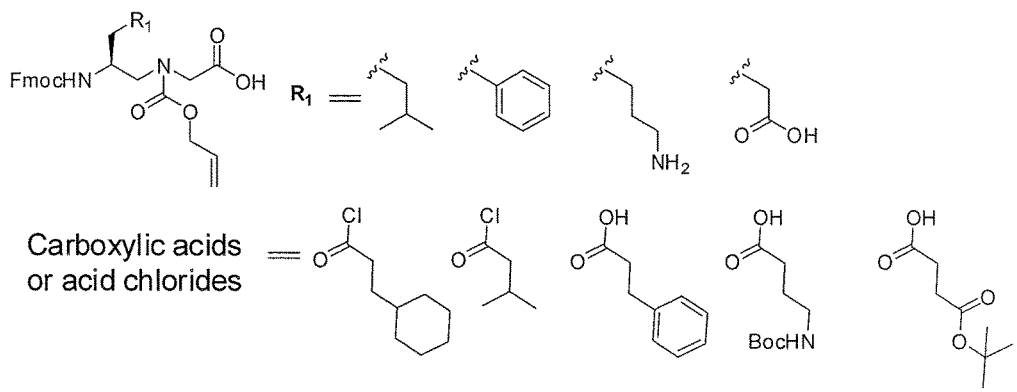
FIG. 4 illustrates embodiments of N-Alloc protected γ-AApeptide building blocks and acylating agents (carboxylic acids and acyl chlorides) that can be used in the preparation of γ-AApeptides of the present disclosure and in the preparation of γ-AApeptide combinatorial ligand libraries.

In the methods of the present disclosure for synthesis of γ-AApeptide compounds and compound libraries, N-alloc protected γ-AApeptide building blocks are designed and obtained following the procedure shown in FIG. 2. The building blocks are used to prepare γ-AApeptides of diverse functional groups (FIGS. 3 and 4). Briefly, on the solid phase, the alloc protecting group is removed by 0.1 equiv $Pd(PPh_3)_4$ and 6 equiv $Me_2NH.BH_3$ in DCM (see Gomez-Martinez, et al., *Journal of the Chemical Society-Perkin Transactions* 1, 2871-2874 (1999) which is hereby incorporated by reference herein for removal of alloc protecting groups), which is found to be efficient and only takes about 10 min to give the product with quantitative conversion. A variety of carboxylic acids or acyl chlorides can then be used to acylate the N on the γ-AApeptide backbone.

Figure 5:
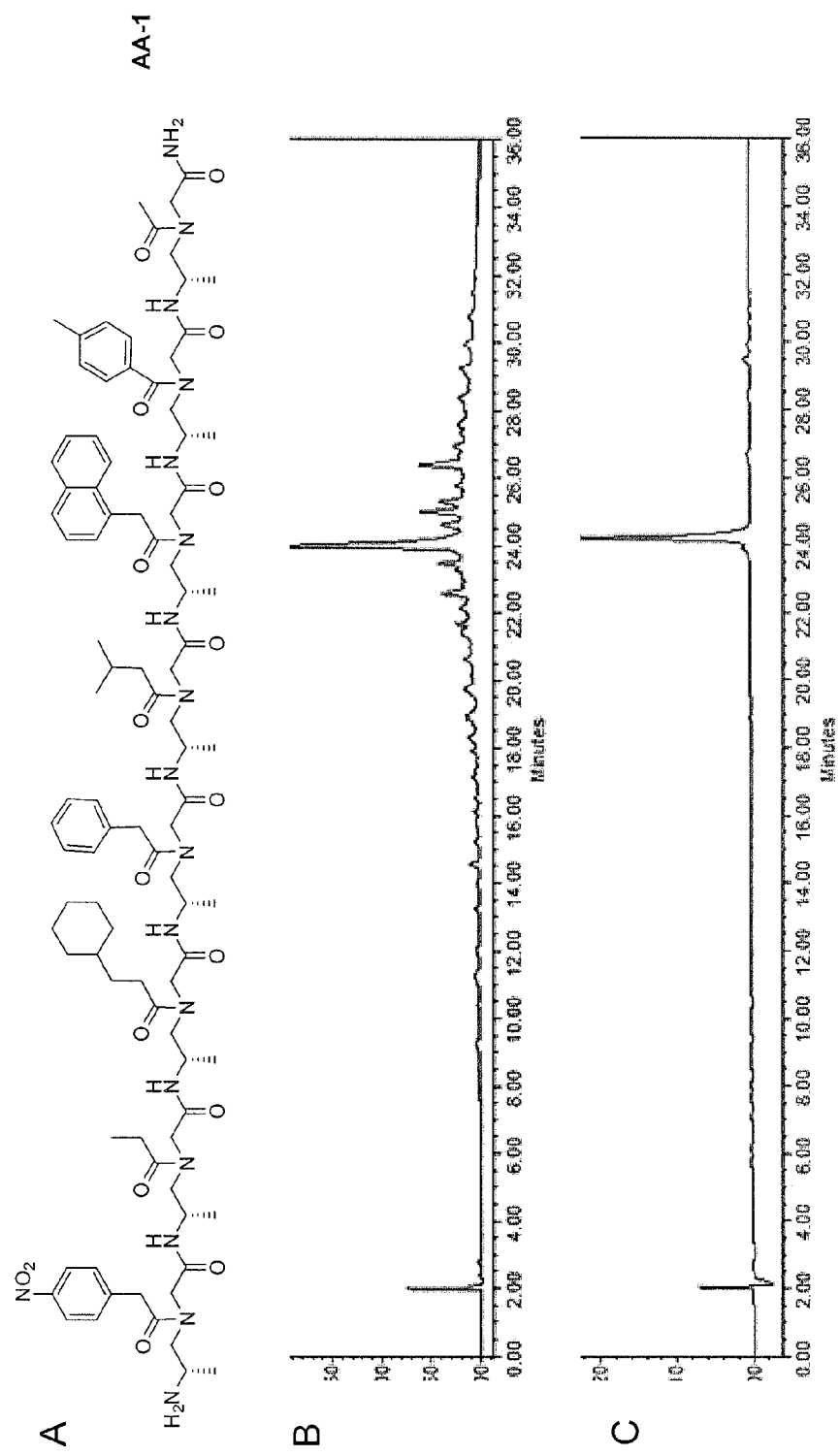
FIGS. 5A-5C illustrate the chemical structure of model compound AA-1 (FIG. 5A), the analytical HPLC trace for crude product (FIG. 5B), and the analytical HPLC trace for purified product (FIG. 5C).

To test the efficiency of this methodology, an 8-building-block γ-AApeptide (comparable to a 16-mer peptide) was synthesized with one N-alloc protected γ-AApeptide building block but derivatized with N-acylated side chains (FIG. 5). The purity of the crude product was found to be around 65%. This is an excellent result as the sequence is much longer than sequences generally used in most ligand libraries. The efficiency of the solid phase synthesis of such a long sequence is comparable to the preparation of regular peptides, even though the synthesis was not protected by any inert gas such as nitrogen or argon. Next, a tetra-block sequence (comparable to an 8-mer peptide) was synthesized with different N-alloc protected γ-AApeptide building blocks derivatized with different N-acylated side chains. The purity of this completely random sequence was >80% (FIG. 6), which demonstrates the feasibility of this approach for the efficient preparation of chemically diverse γ-AApeptides. In this current method, only a few N-alloc protected γ-AApeptide building blocks are needed to prepare γ-AApeptides with virtually limitless functional diversity. In addition, compared to previous approaches, this new approach significantly reduces the steps and shortens the time of synthesis, and greatly improves the yield and purity of γ-AApeptides. Furthermore, N-alloc building blocks have much superior stability to Fmoc-amino aldehydes, the basic units used in the submonomeric synthesis of γ-AApeptides described in Wu, H. et al., *Organic letters* 14, 3446-3449 (2012) (incorporated by reference herein regarding submonomeric synthesis of gamma-AA peptides), making their long-term storage possible. To demonstrate the versatility of this new approach, a γ-AApeptide one-bead-one-compound combinatorial library was made, which is not accessible by previous approaches.

Figure 7:
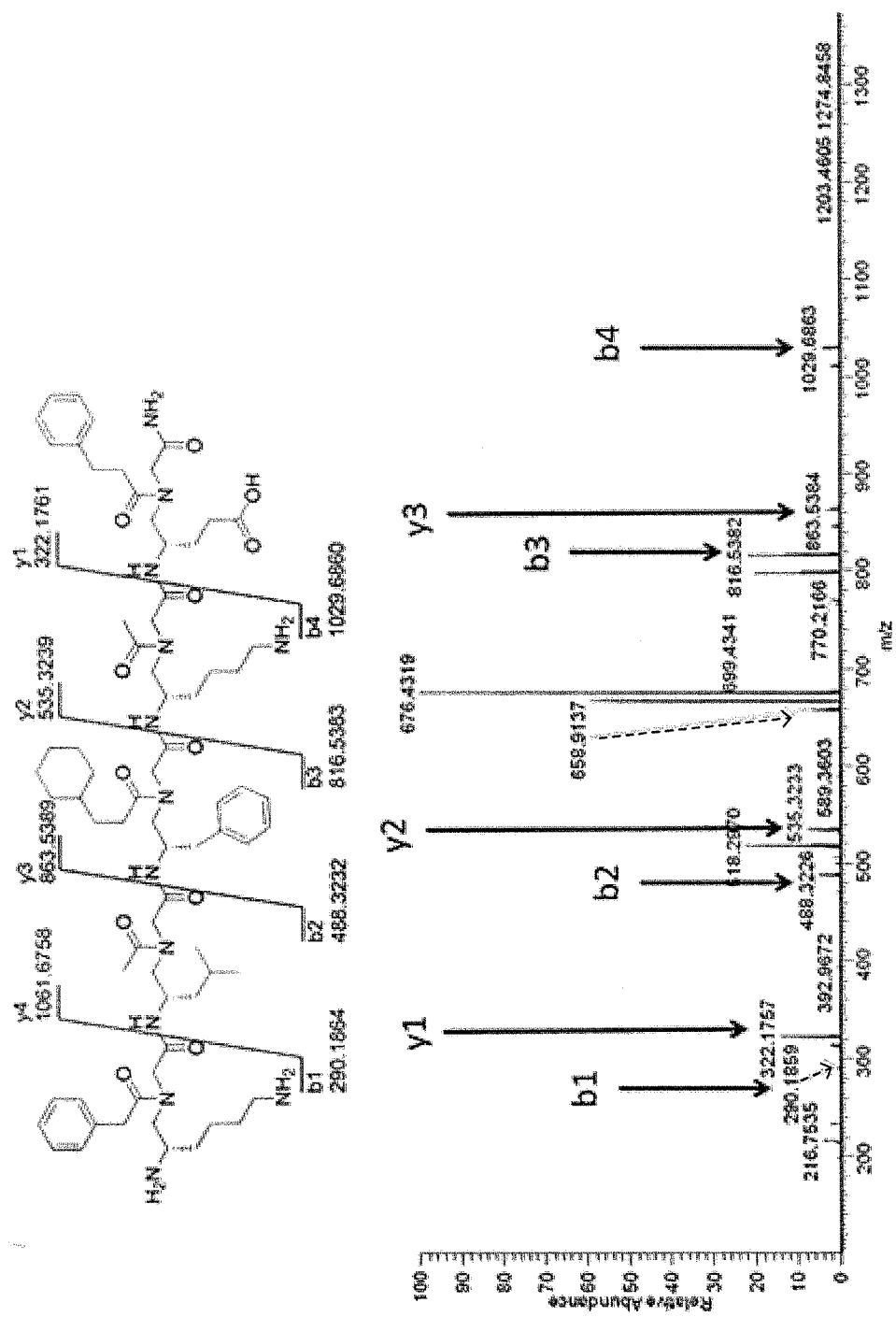
FIG. 7 illustrates the structure and MS/MS analysis of a known γ-AApeptide. HCD fragmentation of a double charged precursor ion was performed at collision energy of 35.

To find out if MS/MS can be potentially used to solve the unknown γ-AApeptide structure, the fragmentation pattern of one known γ-AApeptide was analyzed to prove that MS/MS is capable of determining the sequences of γ-AApeptides. Typically, in this method, Collision Activated Dissociation (CAD) fragments peptides at the amide bond, with other minor fragmentation pathways. As shown in FIG. 7, this γ-AApeptide produces fragments in clear patterns and the sequence can be deduced unambiguously.

Figure 8:
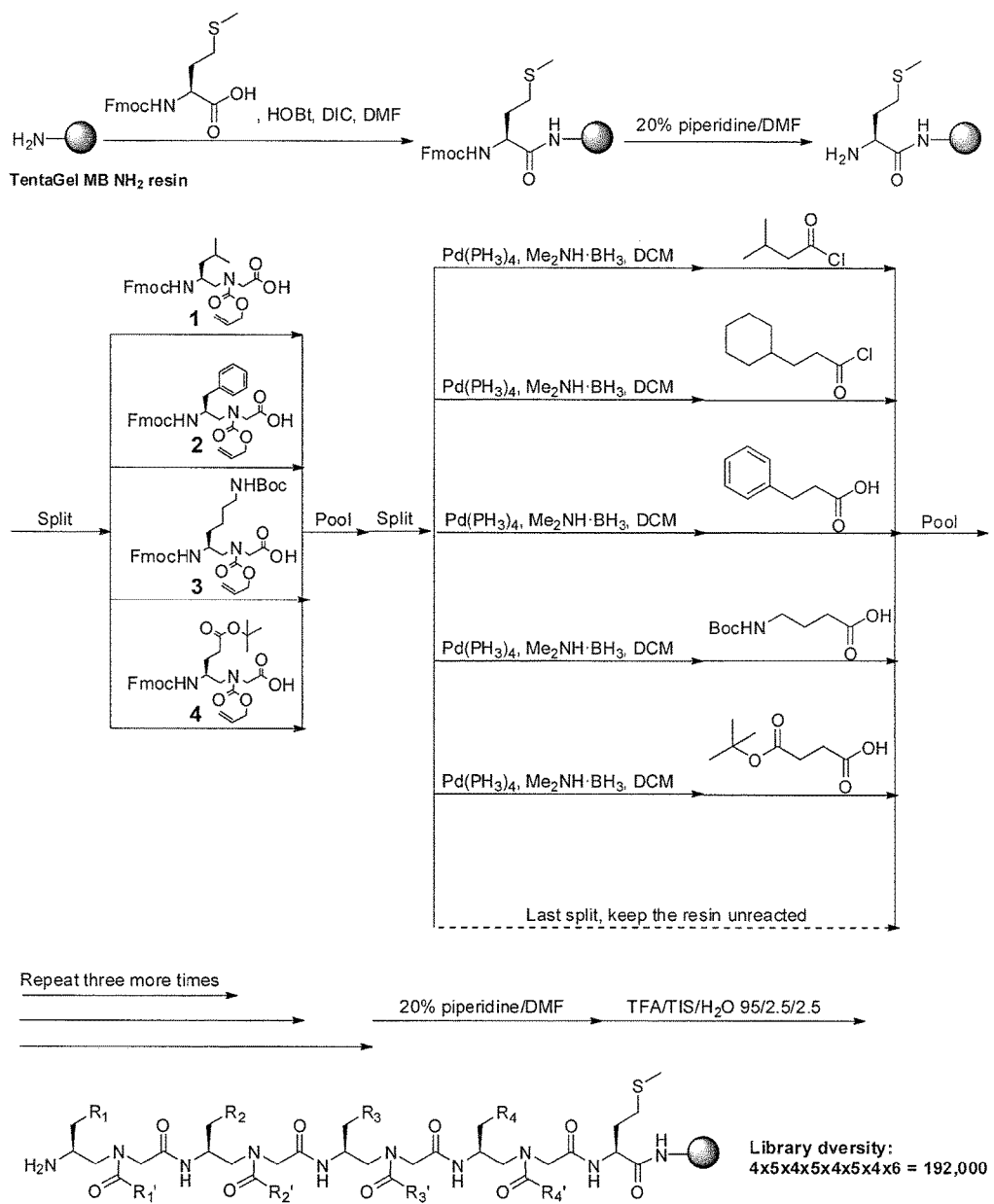
FIG. 8 illustrates scheme 3, a schematic representation of an embodiment of the method of the present disclosure of synthesizing a OBOC ("one-bead-one-compound") γ-AApeptide library.

The next step was to establish a one-bead-one-compound (OBOC) γ-AApeptide library using the new synthetic strategy. The library was prepared by split-and-pool method, which produces beads with only one compound displayed on one bead (Scheme 3, which is illustrated in FIG. 8). A methionine residue was first attached to TentaGel beads (160002, 150 μm, 520, 000 beads/g), which facilitates the cleavage from beads by CNBr treatment (see Aquino, C. et al. *Nature chemistry* 4, 99-104 (2012) which is incorporated by reference herein regarding bead attachment and cleavage). Then 4 N-alloc-protected γ-AApeptide building blocks, and 5 acylating agents (including carboxylic acids or acid chlorides) (FIG. 4) were used to generate the combinatorial library of 4-building-block γ-AApeptides (comparable to 8-mer peptides in length). In theory, this library would contain 4×5×4×5×4×5×4×6=192,000 compounds. After the synthesis was completed, 10 beads were randomly picked up and the sequences were cleaved by CNBr before being analyzed by MS/MS. All the sequences could be determined unambiguously, with one example shown in FIG. 9. The results demonstrate that the quality of this library is excellent, and MS/MS analysis of the γ-AApeptide sequences is straightforward.

To explore the potential of this γ-AApeptide library as an excellent source of protein/peptide ligands, the library was screened against the $A\beta_{40}$ peptide, which is one of the major etiological factors for Alzheimer's disease (AD) and plays a central role in the pathogenesis of AD. It is believed that aggregated forms of $A\beta_{40}$ and $A\beta_{42}$ and the resultant fibrils are a major cause of AD due to their toxicity to neurons. As such, Aβ oligomers and fibrils are a potential target for the treatment of AD, as removal of Aβ fibrils or plaques may eliminate the toxicity of Aβ aggregates. Although it is of high significance to quickly identify novel anti-Aβ aggregation inhibitors, currently no effective approach exists to achieve it.

The hydrophobic core at residues 16-20 of the Aβ peptide, KLVFF (SEQ ID NO: 1, referred to hereinafter as "KLVFF"), has been identified as integral in the formation of Aβ aggregates. Such peptide was shown to bind to Aβ peptides and prevent their aggregation into fibrils. As such, the KLVFF peptide has served as a lead to develop potential therapeutic agents to inhibit Aβ aggregation both in vitro and in vivo. However, KLVFF peptide itself has a weak capability to inhibit Aβ aggregation. Meanwhile, it is susceptible to protease degradation, which further limits its potential development. The effort for the development of inhibitors of Aβ aggregation has also extended to combinatorial chemistry, such as aptamer discovery; however, being fairly large, the identified aptamers do not show capability to prevent Aβ aggregation.

Figure 10:
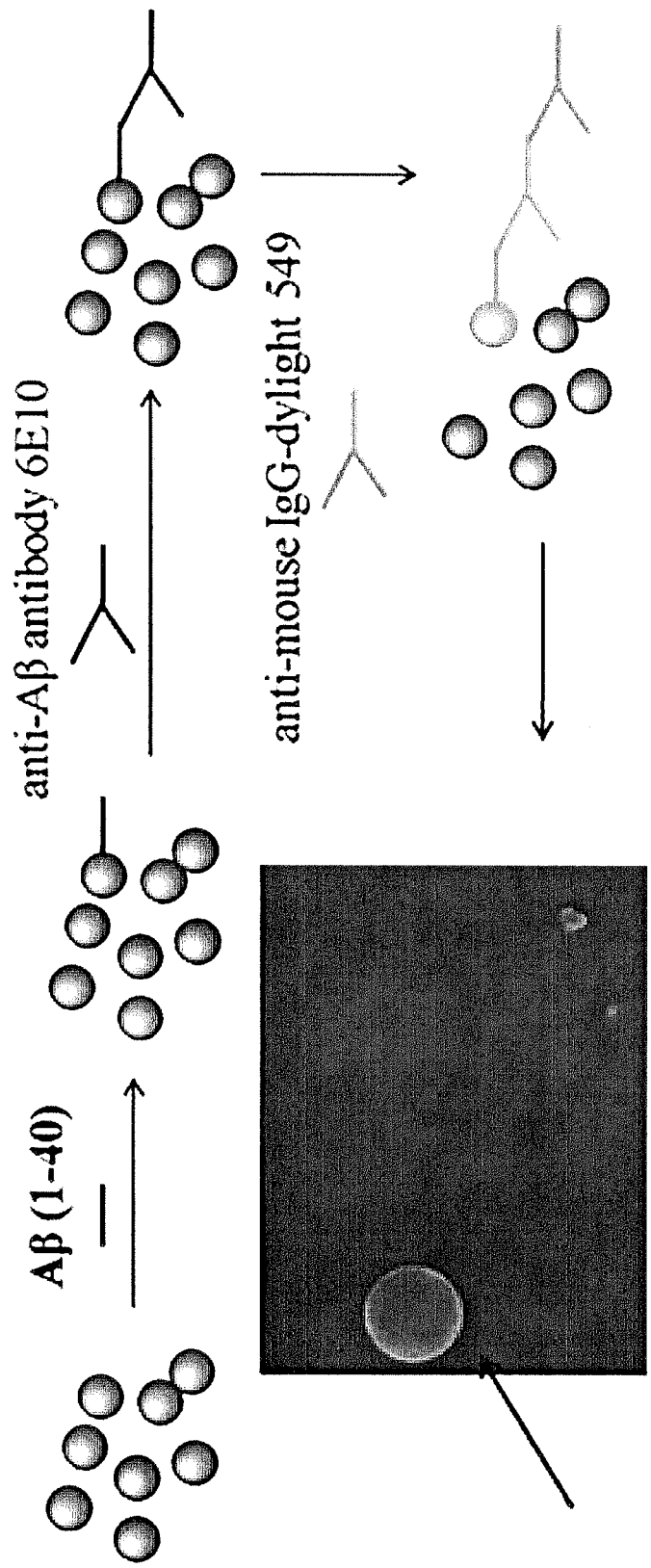
FIG. 10 illustrates a schematic representation of an embodiment of a method of on-bead screening of a γ-AApeptide library against the $A\beta_{40}$ peptide and a digital image of a bead, taken under a fluorescent microscope installed with a triple filter pass; excitation was 550 nm and emission was 605 nm.
Figure 11:
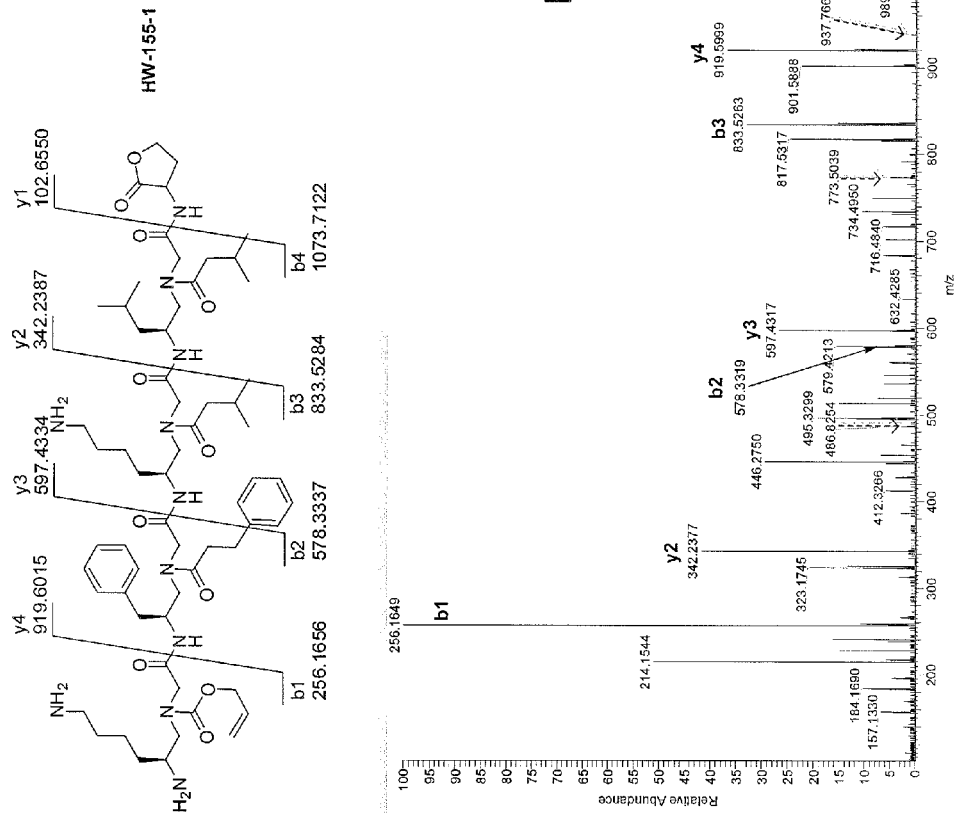
FIG. 11 illustrates the structural identification of one hit (compound HW-155-1) by MS/MS analysis. HCD fragmentation was performed on a double charged precursor ion (587.8827) and the collision energy was set at 35.
Figure 12:
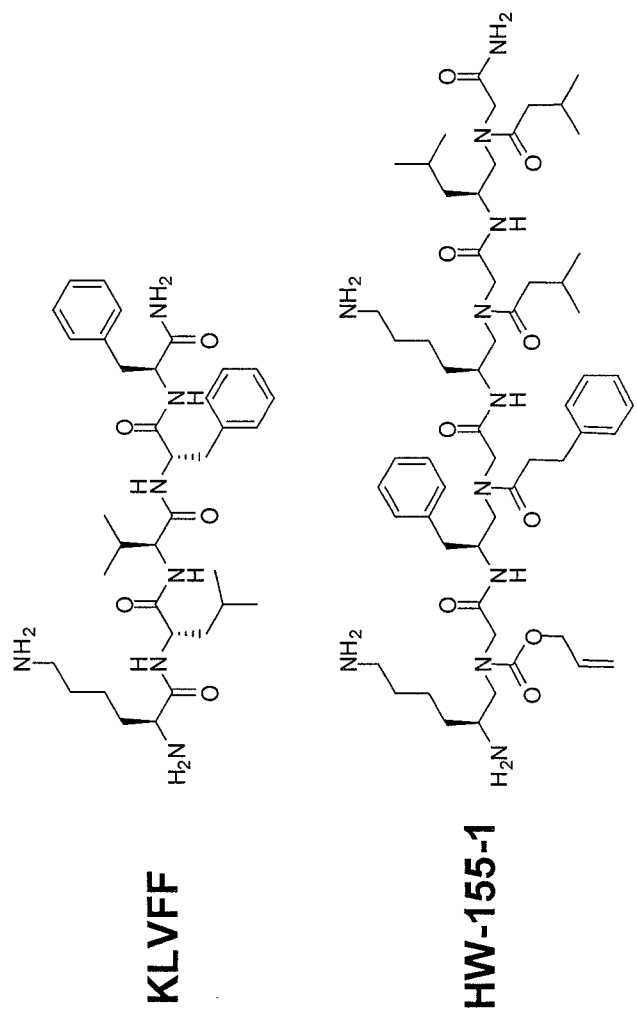
FIG. 12 illustrates the chemical structures of the γ-AApeptide from the on-bead screening (HW-155-1) and the positive control peptide KLVFF (SEQ ID NO: 1, hereinafter referred to as "KLVFF").

The γ-AApeptide library was screened to identify ligands that can bind to Aβ. The anti-aggregation efficiency of identified ligands was determined by functional assay afterwards. Thus, beads were incubated with the $A\beta_{40}$ peptide, followed by the treatment of anti-Aβ antibody 6E10 (FIG. 10). Then, anti-mouse IgG-dylight 549 conjugate was added. Dylight 549 produces strong orange fluorescence, a region in which TentaGel beads have low background fluorescence (see Aquino, C. supra, 4, which is incorporated by reference herein regarding properties of TentaGel beads). The dye is also much less expensive than quantum dots. Out of ~192,000 beads, two putative hits (approximately 0.001% hit rate) were identified and collected. The low rate may suggest the high selectivity of the library. One of the structures was identified by MS/MS unambiguously (FIG. 11). This lead, designated as HW-155-1, was re-synthesized on Rink-amide resin (FIG. 12). The peptide KLVFF was also synthesized and used for comparison. HPLC was determined for HW-155-1 and KLVFF (FIGS. 13A and 13B, respectively) for comparison, as described in the methods below.

Figure 14:
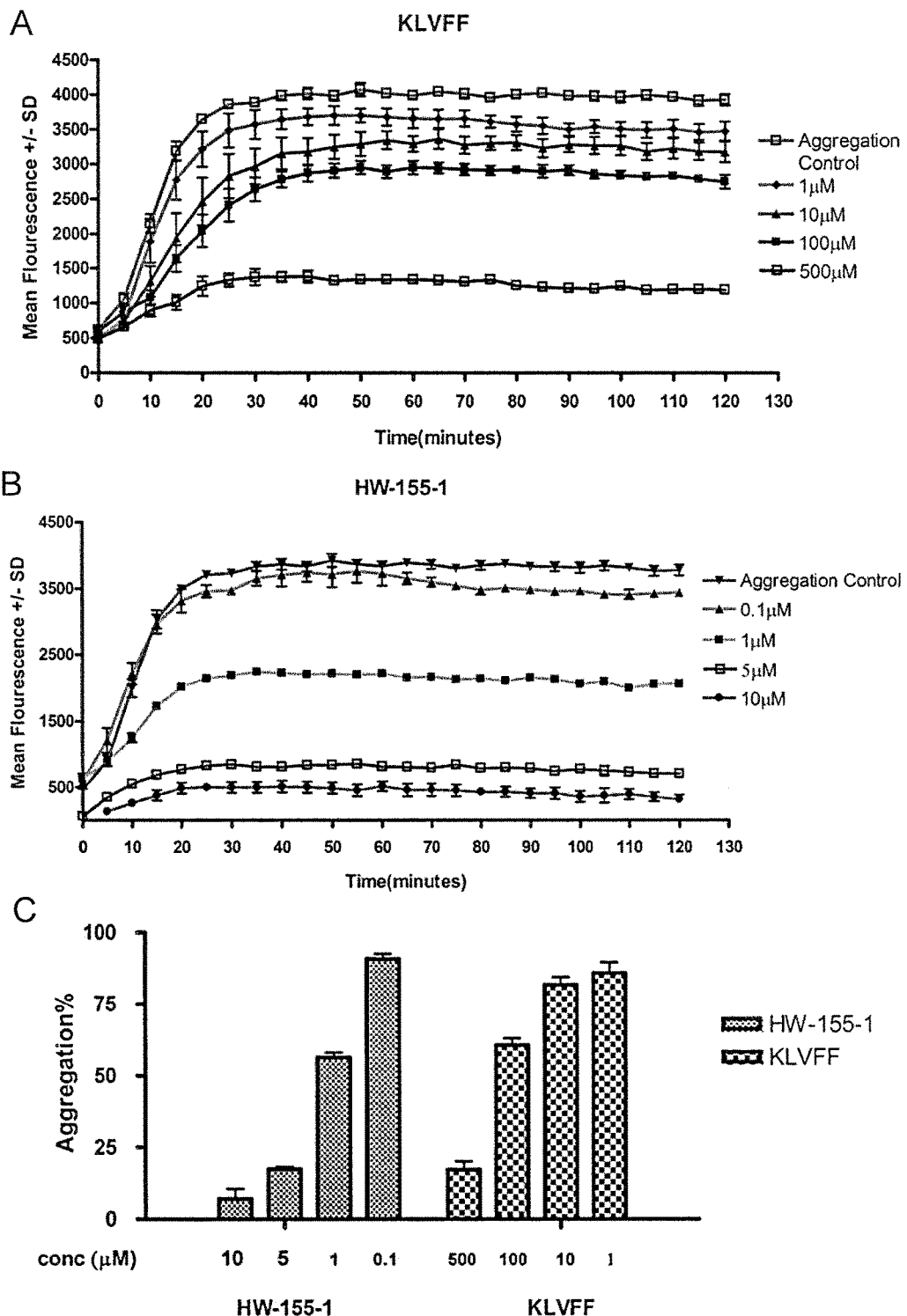
FIGS. 14A-14C is a series of graph illustrating a ThT assay of compounds against $A\beta_{40}$. The graph of FIG. 14A shows the change of fluorescence in the first 2 h of incubation of KLVFF with $A\beta_{40}$; the graph of FIG. 14B shows the change of fluorescence in the first 2 h of incubation of HW-155-1 with $A\beta_{40}$.

These two sequences were investigated for their capability to inhibit the aggregation of $A\beta_{40}$ by ThT assay. Consistent to previous reports, KLVFF is the weak disruptor of Aβ aggregates. 100 μM of KLVFF can only inhibit less than 50% of Aβ aggregation (FIG. 14A). Surprisingly, 1 μM of HW-155-1 already inhibits ~50% of Aβ aggregation (FIG. 14B), indicating it is at least 100-fold more potent than KLVFF. The similar inhibitory effect was observed even after 24 h (FIG. 14C). As such, HW-155-1 is one of the most potent small molecules that disrupt the aggregation of Aβ40.

Figure 15:
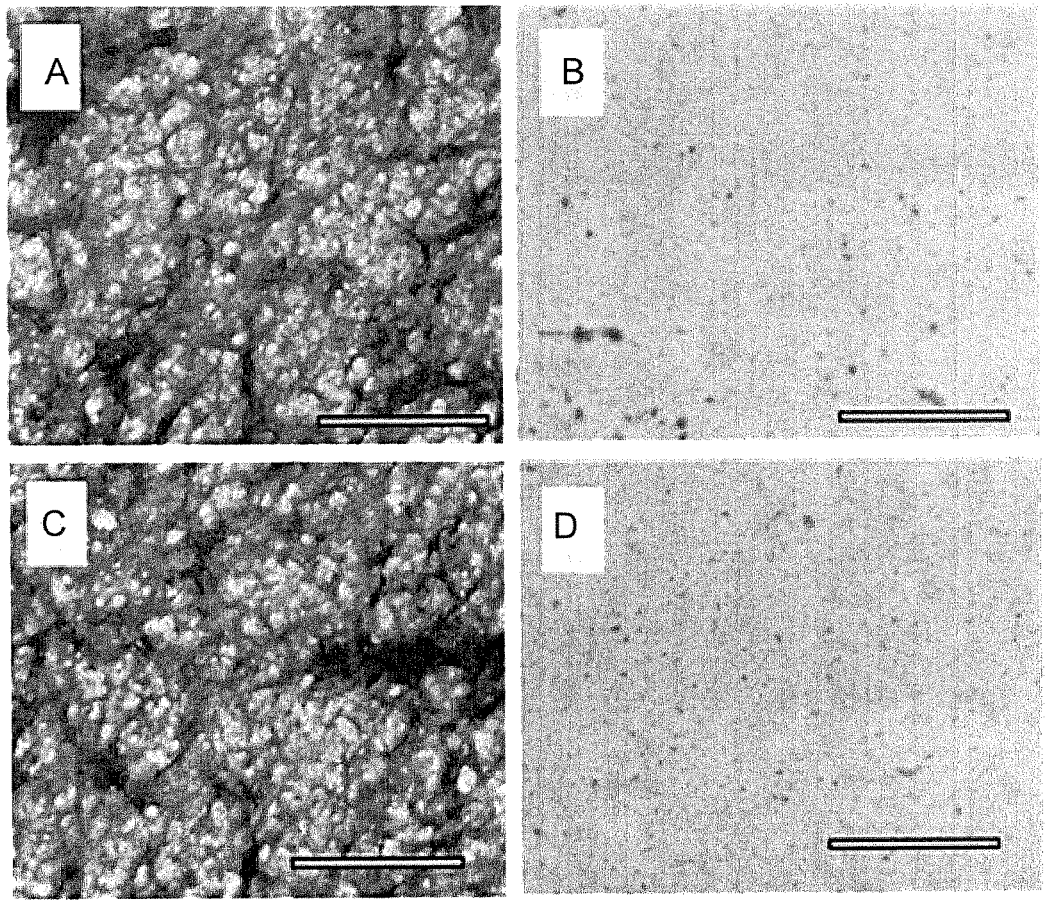
FIGS. 15A-15D are TEM images illustrating monomeric $A\beta_{40}$ in the absence (FIG. 15A) and presence (FIG. 15B) of HW-155-1 after 24 h and pre-aggregated $A\beta_{40}$ in the absence (FIG. 15C) and presence (FIG. 15D) of HW-155-1 after 24 h. Bar=1 μM; $A\beta_{40}$ is 2.5 μM; and HW-155-1 is 5 μM.

The ability of HW-155-1 to prevent Aβ aggregation was further confirmed by TEM (FIGS. 15A and 15B). In fact, HW-155-1 can even disassemble pre-formed Aβ fibrils (FIGS. 15C and 15D). In these experiments, the Aβ fibrils were not seen for 24 h after incubating HW-155-1 with $A\beta_{40}$ monomers (prevention of aggregation) and pre-formed $A\beta_{40}$ aggregates (disassembling aggregation).

Figure 16:
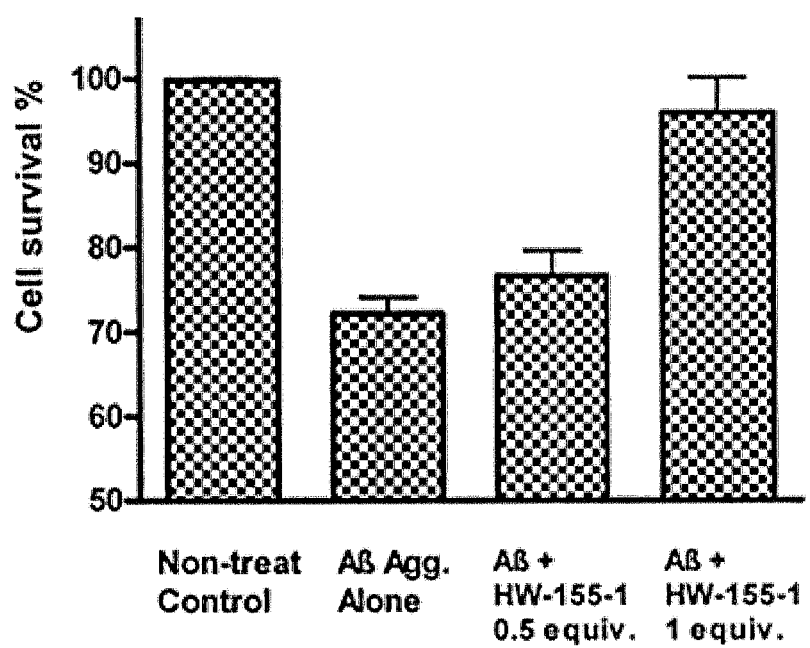
FIG. 16 is a bar graph illustrating detoxification of $A\beta_{42}$ aggregates by HW-155-1. N2a cells were cultured with 1 μM of pre-aggregated $A\beta_{42}$ in the absence/presence of HW-155-1 for 24 h.
Figure 17A:
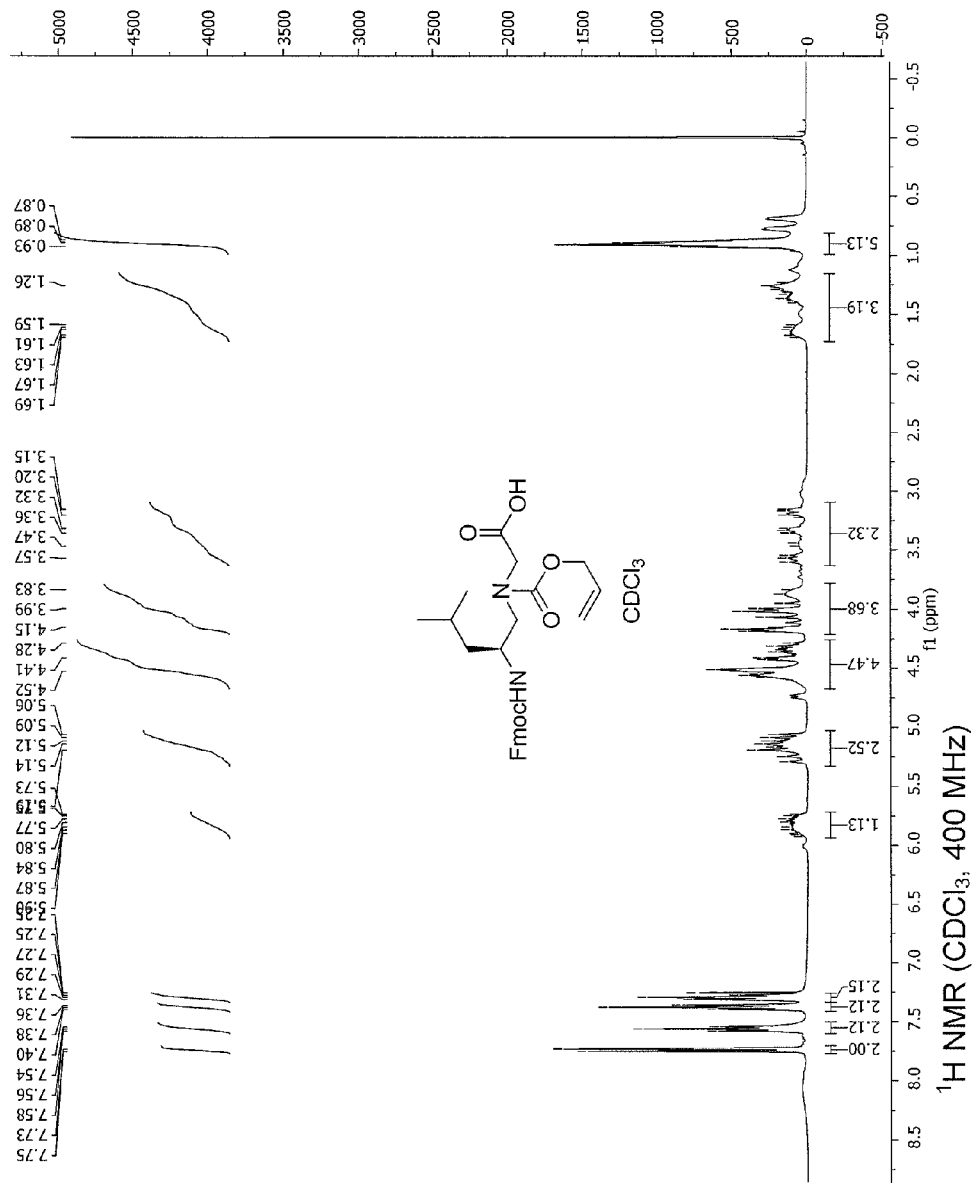
FIGS. 17A-B illustrate the CNMR (FIG. 17A) and HNMR (FIG. 17B) for the building block compound 1, structure shown.
Figure 17B:
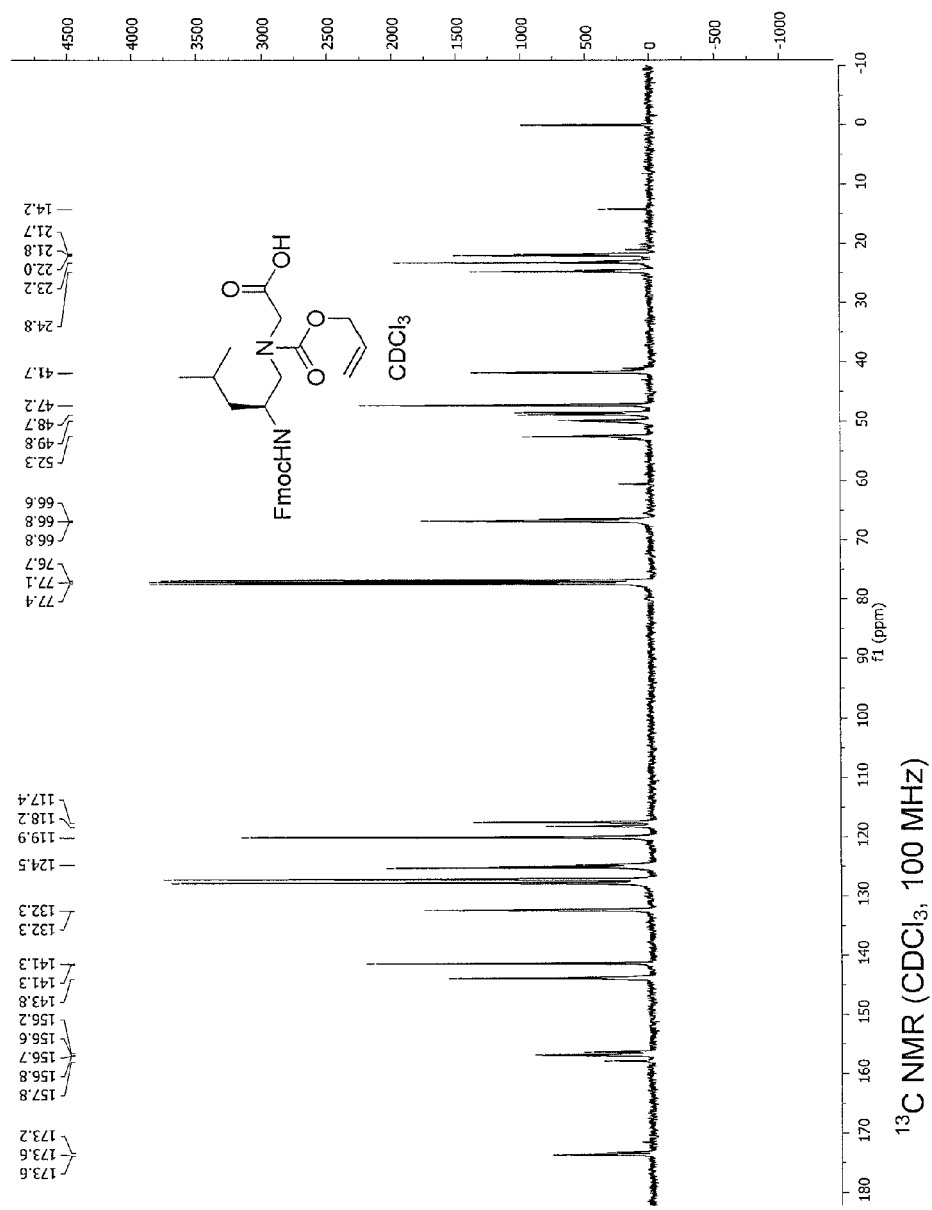
Figure 18A:
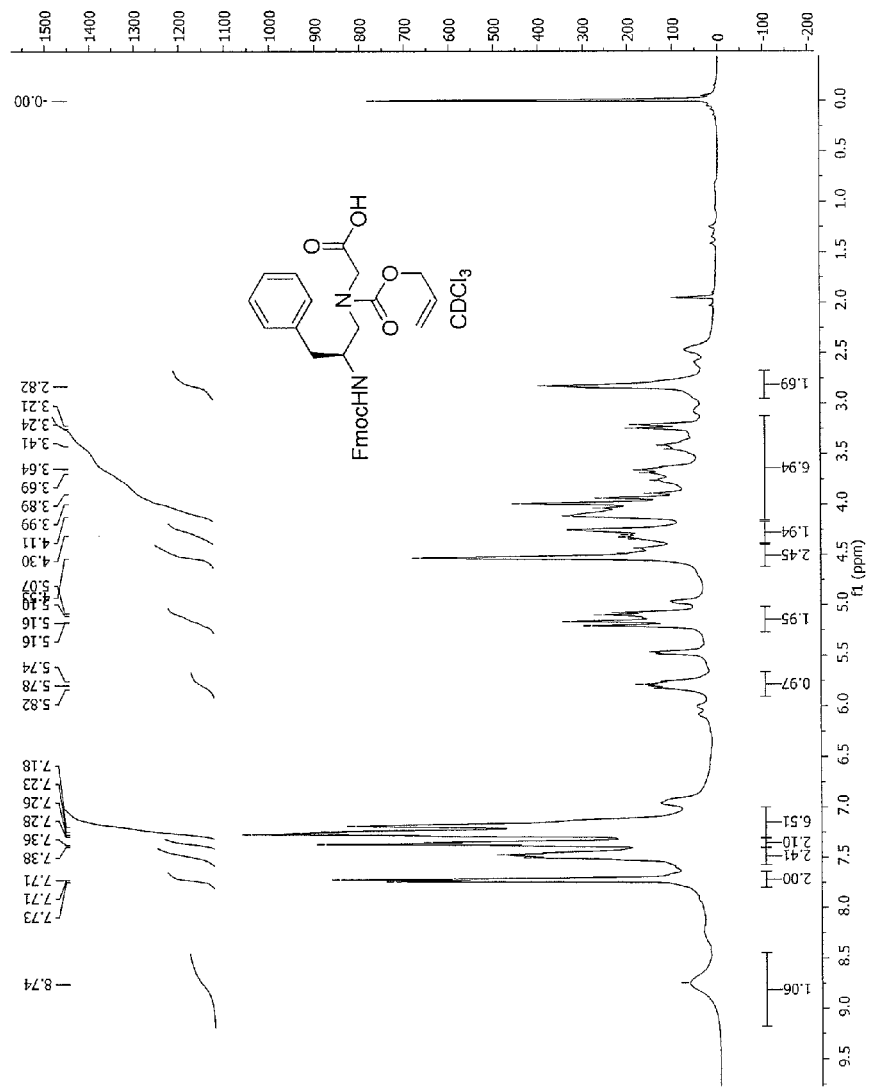
FIGS. 18A-18B illustrate the CNMR (FIG. 18A) and HNMR (FIG. 18B) for the building block compound 2, structure shown.
Figure 18B:
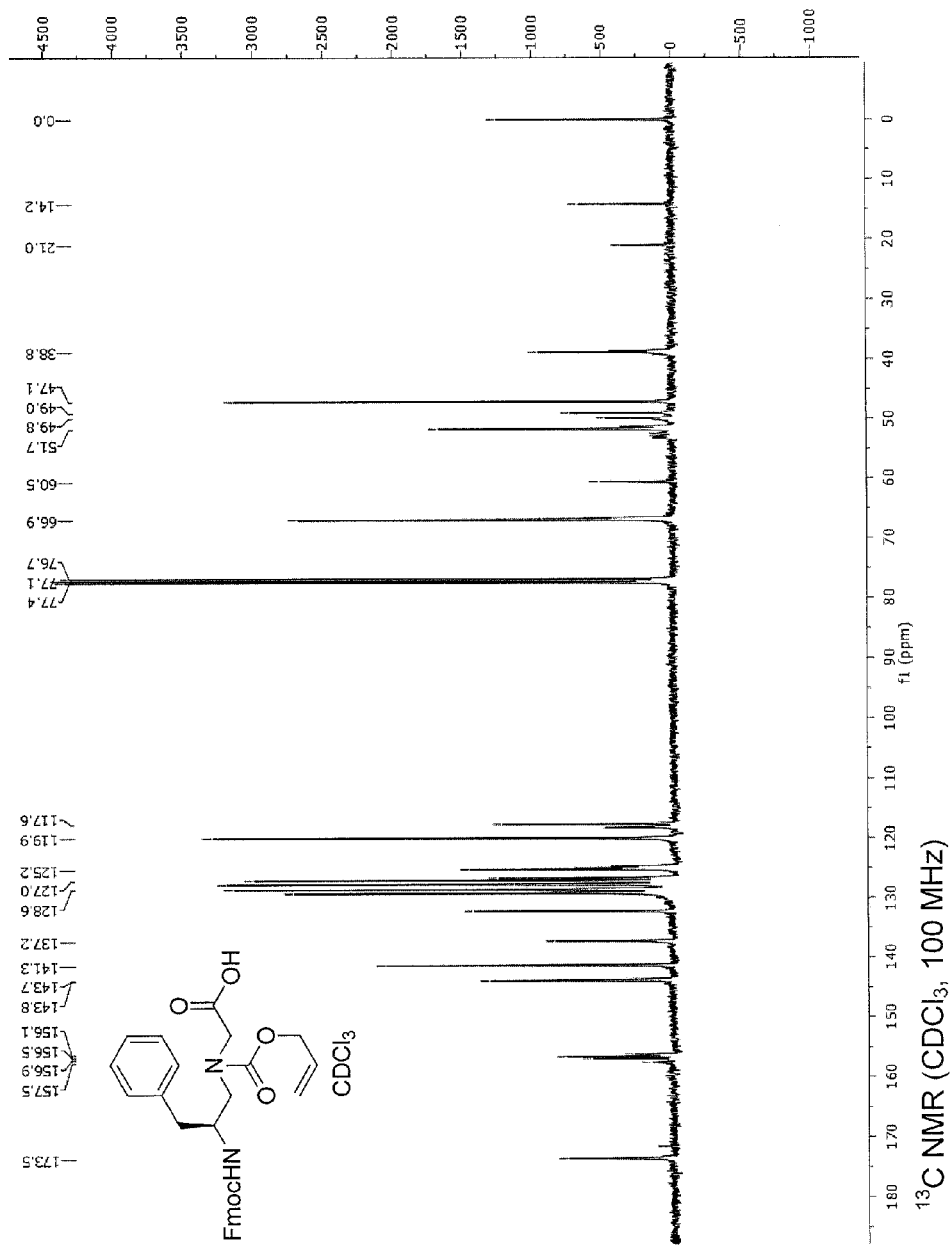
Figure 19A:
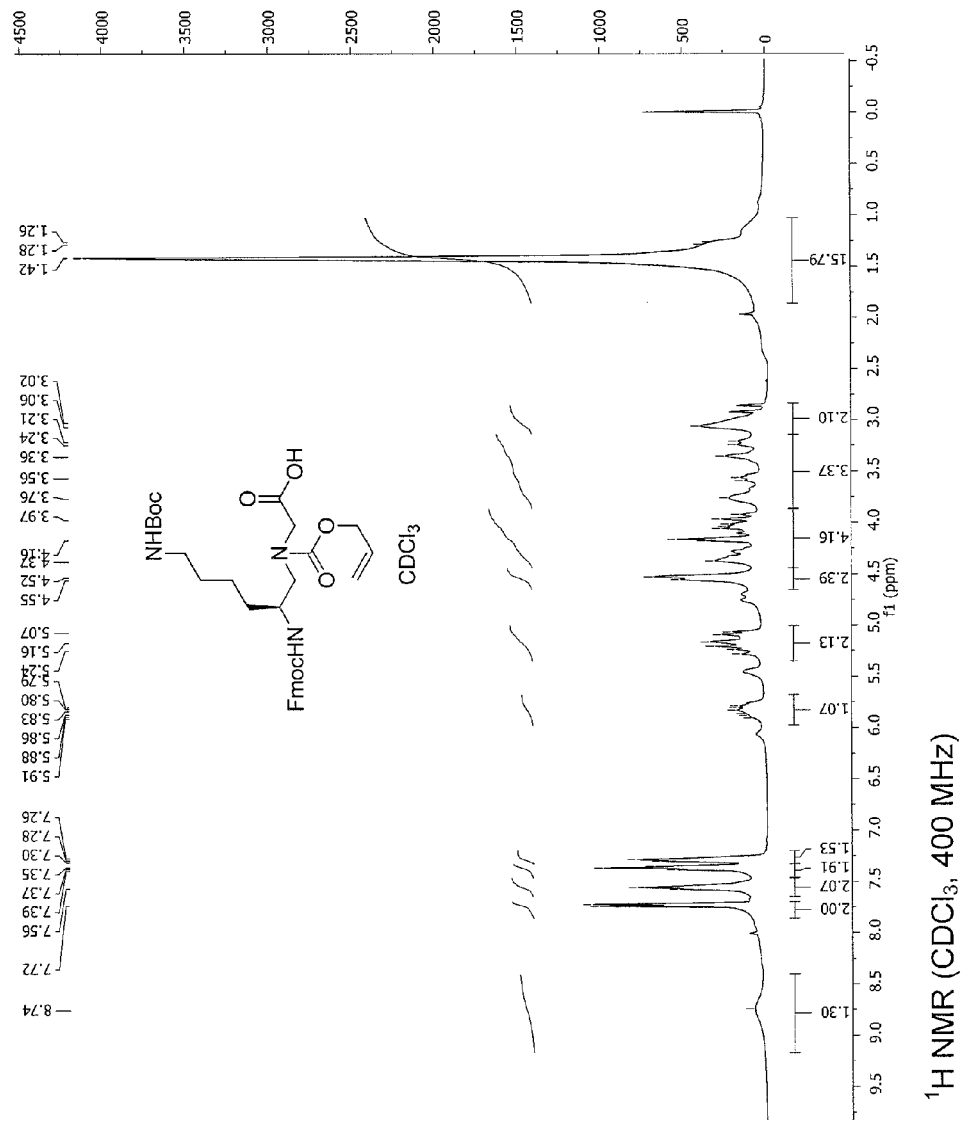
FIGS. 19A-19B illustrate the CNMR (FIG. 19A) and HNMR (FIG. 19B) for the building block compound 3, structure shown.
Figure 19B:
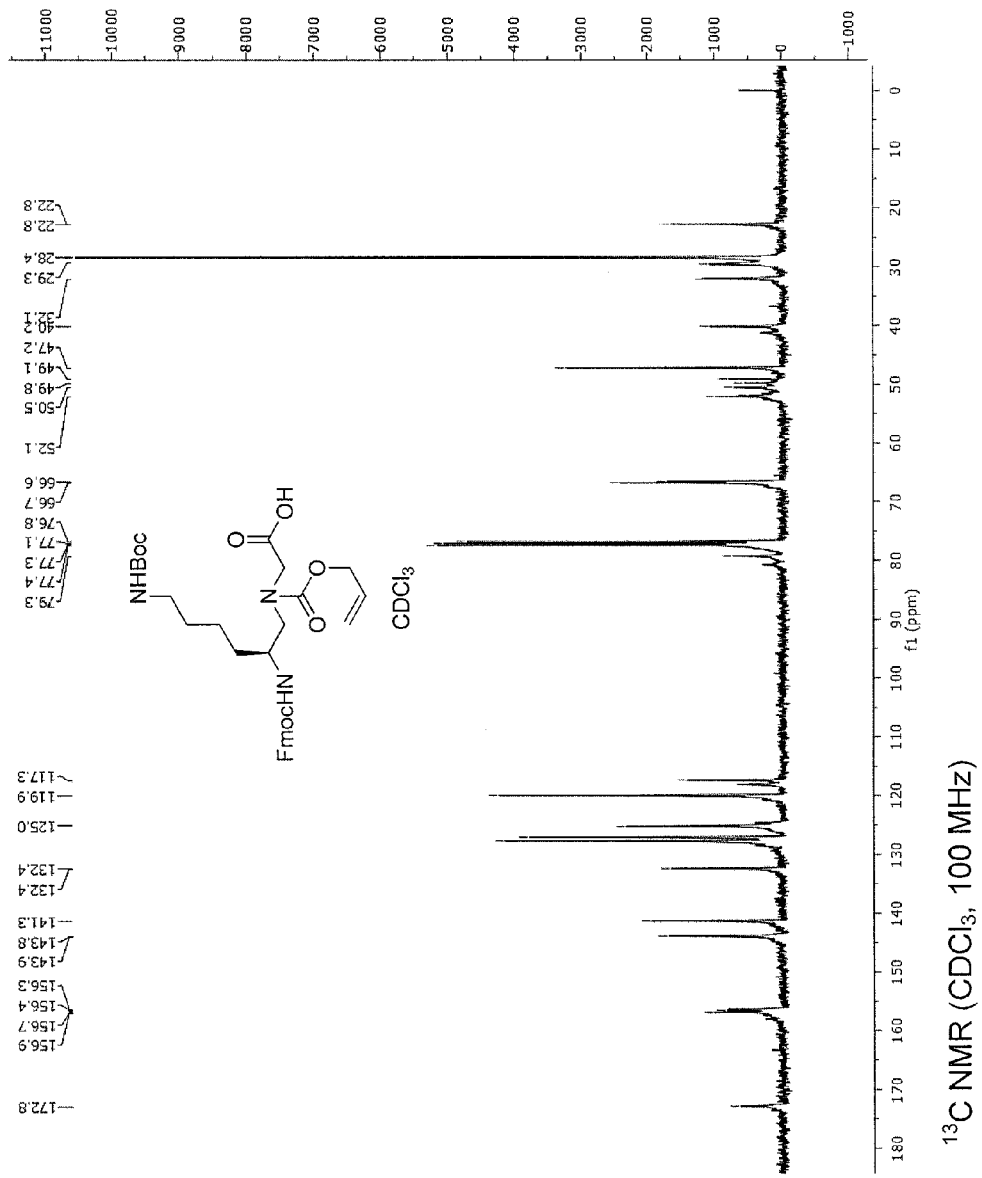
Figure 20A:
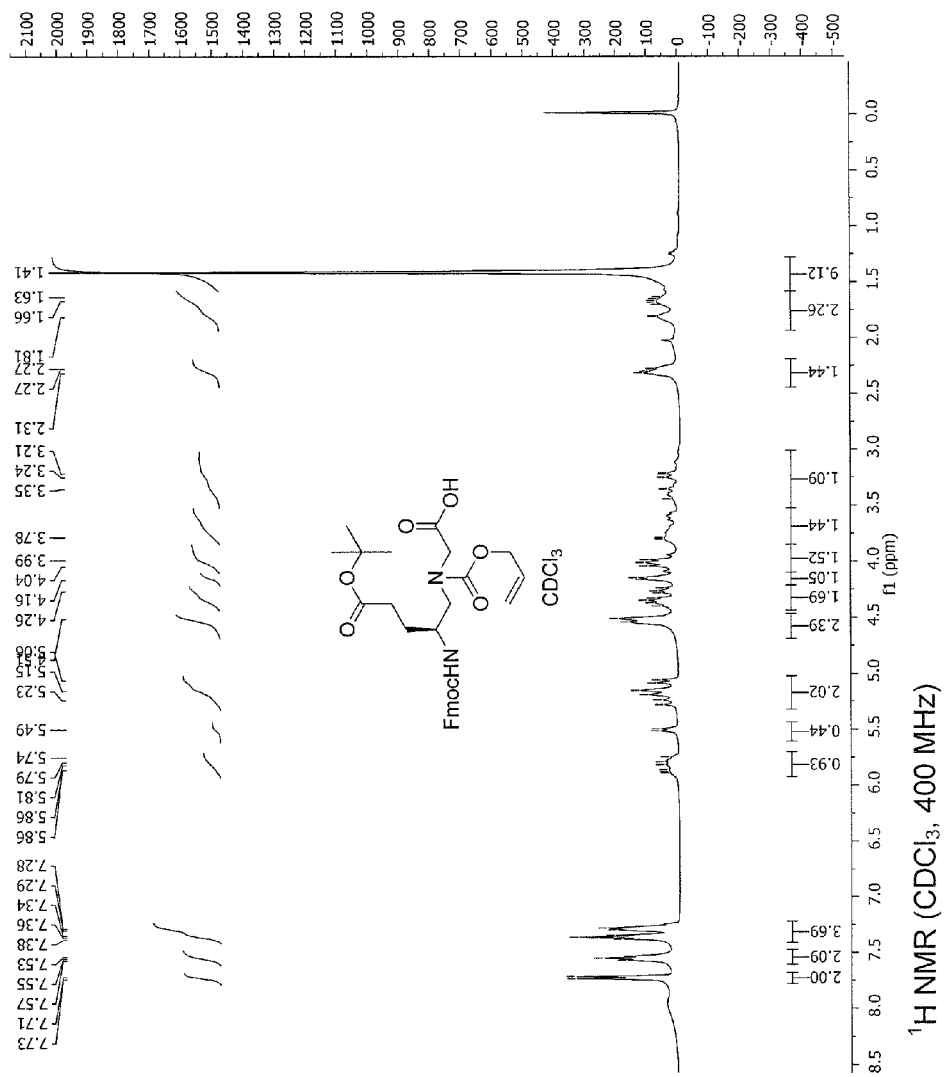
FIGS. 20A-20B illustrate the CNMR (FIG. 20A) and HNMR (FIG. 20B) for the building block compound 4, structure shown.
Figure 20B:
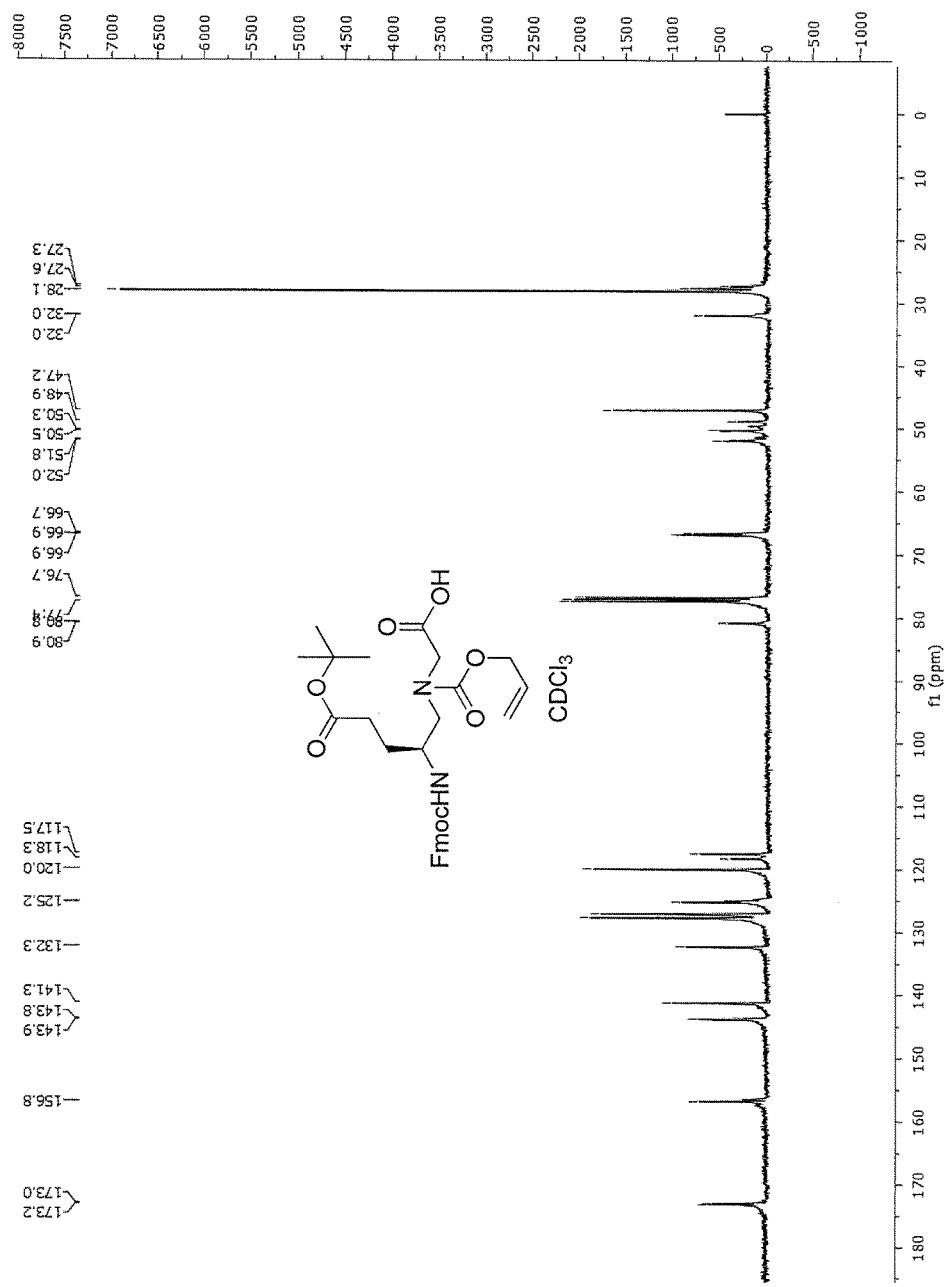

The effect of HW-155-1 on the toxicity of Aβ aggregates towards N2a neuroblastoma cells was then examined. In this cellular assay, $A\beta_{42}$ was chosen because $A\beta_{42}$ aggregates are easier to form and are more toxic than $A\beta_{40}$ aggregates towards neural cells.[36,42] As shown in FIG. 16, pre-incubated $A\beta_{42}$ kills 30% of N2a cells. In contrast, pre-incubation of 0.5 equiv. of HW-155-1 with $A\beta_{42}$ reduces the death of N2a cells to 25%, while the presence of 1 equiv. HW-155-1 almost completely removes the toxicity of $A\beta_{42}$ and virtually eliminates the death of N2a cells. The capability of HW-155-1 to rescue these neuroblastoma cells suggests that HW-155-1 prevents the formation of Aβ aggregates and thus decreases the Aβ toxicities.

Conclusions

In summary, this example demonstrates the production of a new class of peptidomimetic combinatorial library that shows great promise as a rich source of protein/peptide ligands. γ-AApeptides have a unique backbone that allows introduction of diverse functional groups with virtually limitless potential. Their similarity in size and chirality to canonical peptides also confers favorable characteristics to bind and interact with other peptides and proteins. The new, synthetic approach reported here has realized the potential of γ-AApeptides towards combinatorial development, as now γ-AApeptides with virtually any functional groups can be synthesized at high efficiency and ease. As demonstrated, the new synthetic strategy is highly compatible to the split-and-pool solid phase synthesis to generate novel one-bead-one-compound γ-AApeptide libraries. As such, large libraries are expected to be accessible with ease and inexpensive efforts, which circumvents the drawbacks associated with the traditional high-throughput screening such as dedicated infrastructure and low efficiency.

Moreover, this initial effort with the novel library prepared in the present example has led to the identification of a lead small γ-AApeptide that effectively prevents and even disrupts Aβ aggregation, and removes the toxicity of Aβ aggregates towards N2a neuroblastoma cells. Such a compound may be used as a potential molecular probe or therapeutic agent for the treatment of Alzheimer's disease (AD).

Experimental Materials and Procedures:
Library Synthesis
1. General Information

All Fmoc protected α-amino acids and Rink amide resin (0.7 mmol/g, 200-400 mesh) were purchased from Chem-Impex International, Inc. TentaGel MB $NH_2$ resin (0.3 mmol/g, 140-170 μm) was purchased from RaPP Polymere GmbH. All the other solvents and reagents were purchased from either Sigma-Aldrich or Fisher Scientific. NMR data for building blocks was obtained on a Varian UnityInova400 spectrometer. High resolution masses of building blocks were determined on an Agilent 6540 Liquid Chromatography/Quadrupole Time-of Flight mass spectrometer. Masses of γ-AApeptides were obtained on an Applied Biosystems 4700 Proteomics Analyzer. MS/MS analysis was carried out with a Thermo LTQ Orbitrap XL. Solid phase synthesis was conducted in peptide synthesis vessels on a Burrell Wrist-Action shaker. γ-AApeptides were analyzed and purified on a Waters Breeze 2 HPLC system, and then lyophilized on a Labcono lyophilizer.

2. Preparation of γ-AApeptide Building Blocks

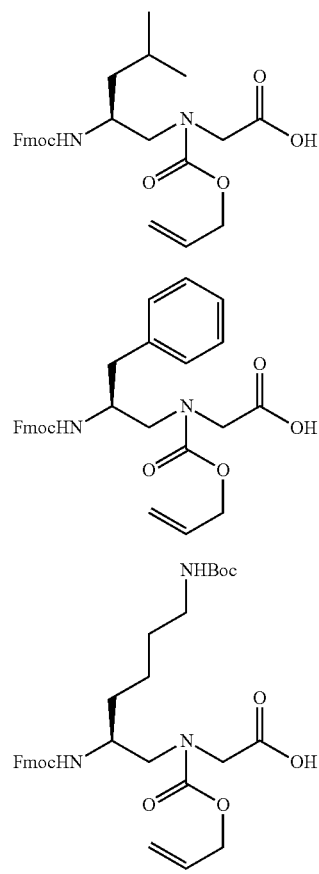

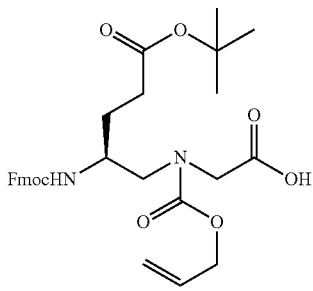

Building blocks used for synthesizing OBOC γ-AApeptide library.

Scheme 1A (an embodiment of Scheme 1, Figure 2). Synthetic route for Lysine and Glutamic acid based γ-AApeptide building blocks (3 and 4).

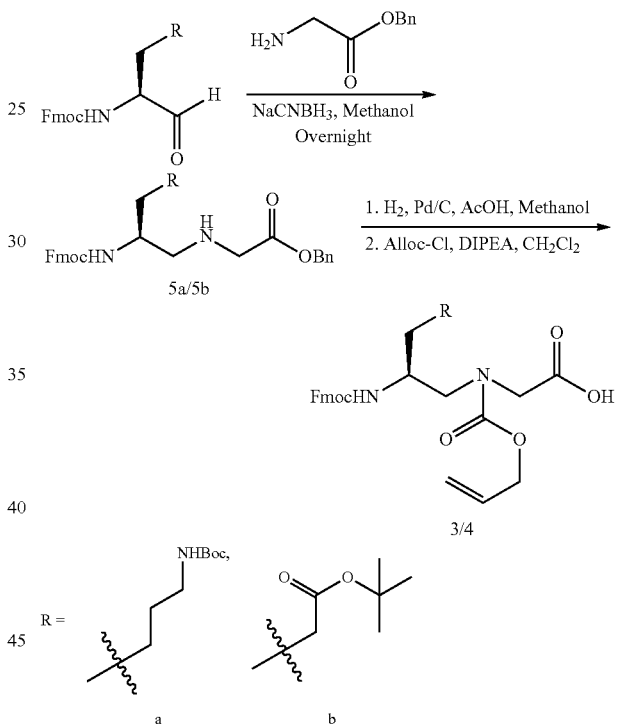

Building blocks 1, 2 and intermediate 5a/5b were synthesized following previously reported methods (Niu, Y. H., et al., J. F. New J Chem 2011, 35, 542; Niu, Y. H., et al., Org Biomol Chem 2011, 9, 6604), which are hereby incorporated by reference herein for synthesis.

Building block 3 was synthesized as shown in Scheme 1A. To a solution of intermediate 5a (2 g, 1.66 mmol) in 50 mL methanol containing 1% acetic acid, Pd/C (0.2 g, 10% wt) was added. Hydrogenation was conducted at atmospheric pressure and room temperature for 2 h. After filtration and evaporation of solvent, the resulting solid was suspended in 50 mL $CH_2Cl_2$ and N, N-diisopropylethylamine (434 μL, 2.49 mmol, 1.5 eqiv.) was added. The solution was cooled to 0° C., then a solution of allyl chloroformate (176 μL, 1.66 mmol, 1 eqiv.) in $CH_2Cl_2$ was slowly added over 1 h. The reaction mixture was allowed to react at room temperature for two more hours, and then washed with saturated citric acid (30 mL×3) and brine solution, dried over Na$_2$SO$_4$, and concentrated under vacuum. The pure building block 3 was obtained as a white foam solid by flash chromatography with 10% MeOH/CH$_2$Cl$_2$ (1.68 g, 85% yield).

Building block 4 was synthesized following the same procedure.

CNMR and HNMR for each of the building block compounds 1-4 are shown in supplemental FIGS. 117A, 17B, 18A, 18B, 19A, 19B, 20A, and 20B.

Compound 1. Yield 65%. $^1$H NMR (CDCl$_3$, 400 MHz) δ (two rotamers) 7.74 (d, J=8 Hz, 2H), 7.56 (t, J=8 Hz, 2H), 7.38 (t, J=8 Hz, 2H), 7.29 (t, J=8 Hz, 2H), 5.92-5.73 (m, 1H), 5.29-5.06 (m, 2H), 4.57-4.28 (m, 5H), 4.17-3.83 (m, 3H), 3.60-3.15 (m, 2H), 1.69-1.23 (m, 3H), 0.93-0.87 (m, 6H) ppm. $^{13}$C NMR (CDCl$_3$, 100 MHz) δ (two rotamers) 173.6, 173.2, 157.8, 156.8, 156.7, 156.6, 156.2, 143.8, 141.3, 132.3, 124.5, 119.9, 118.2, 117.4, 66.8, 66.6, 52.3, 49.8, 48.7, 47.2, 41.7, 24.8, 23.2, 22.0, 21.8, 21.7, 14.2 ppm. HR-ESI: [M+H]$^+$ calc: 481.2333. found: 481.2352.

Compound 2. Yield 61%. $^1$H NMR (CDCl$_3$, 400 MHz) δ (two rotamers) 8.74 (s, 1H), 7.73 (d, J=8 Hz, 2H), 7.50-7.47 (m, 2H), 7.36 (t, J=8 Hz, 2H), 7.28-7.18 (m, 7H), 5.82-5.74 (m, 1H), 5.21-5.07 (m, 2H), 4.53-4.43 (m, 2H), 4.34-4.25 (m, 2H), 4.11-3.21 (m, 6H), 2.82 (s, 2H) ppm. $^{13}$C NMR (CDCl$_3$, 100 MHz) δ (two rotamers) 173.5, 157.5, 156.9, 156.5, 156.1, 143.8, 143.7, 141.3, 137.2, 132.2, 129.2, 129.1, 128.6, 127.7, 127.0, 126.7, 125.2, 119.9, 117.6, 66.9, 60.5, 51.7, 49.8, 49.0, 47.1, 38.8, 21.0, 14.2 ppm. HR-ESI: [M+H]$^+$ calc: 515.2177. found: 515.2196.

Compound 3. Yield 85% (from intermediate 5a). $^1$H NMR (CDCl$_3$, 400 MHz) δ (two rotamers) 8.74 (s, 1H), 7.73 (d, J=8 Hz, 2H), 7.57 (d, J=8 Hz, 2H), 7.37 (t, J=8 Hz, 2H), 7.28 (t, J=8 Hz, 2H), 5.91-5.79 (m, 1H), 5.28-5.07 (m, 2H), 4.55-4.52 (m, 2H), 4.37-3.92 (m, 5H), 3.92-3.21 (m, 3H), 3.06-3.02 (m, 2H), 1.42-1.26 (m, 15H) ppm. $^{13}$C NMR (CDCl$_3$, 100 MHz) δ (two rotamers) 172.8, 156.9, 156.7, 156.4, 156.3, 143.9, 143.8, 141.3, 132.4, 125.0, 119.9, 117.3, 79.3, 76.8, 66.7, 66.6, 52.1, 50.5, 49.8, 49.1, 47.2, 40.2, 32.1, 29.3, 28.4, 22.8 ppm. HR-ESI: [M+Na]$^+$ calc: 618.2786. found: 618.2810.

Compound 4. Yield 88% (from intermediate 5b). $^1$H NMR (CDCl$_3$, 400 MHz) δ (two rotamers) 7.72 (d, J=8 Hz, 2H), 7.56 (d, J=8 Hz, 2H), 7.38-7.28 (m, 4H), 5.88-5.74 (m, 1H), 5.50 (d, J=8 Hz, 1H), 5.28-5.06 (m, 2H), 4.54-4.51 (m, 2H), 4.40-4.24 (m, 2H), 4.16-4.11 (m, 1H), 4.04-3.99 (m, 2H), 3.80-3.78 (m, 2H), 3.44-3.21 (m, 1H), 2.31-2.27 (m, 2H), 1.81-1.63 (m, 2H), 1.41 (s, 9H) ppm. $^{13}$C NMR (CDCl$_3$, 100 MHz) δ (two rotamers) 173.2, 173.0, 156.8, 143.9, 143.8, 141.3, 132.3, 127.7, 127.1, 125.2, 120.0, 118.3, 117.5, 80.9, 80.8, 66.9, 66.7, 52.0, 51.8, 50.3, 48.9, 47.2, 32.0, 28.1, 27.6, 27.3 ppm. HR-ESI: [M+H]$^+$ calc: 553.2544. found: 553.2572.

3. Solid Phase Synthesis of γ-AApeptides

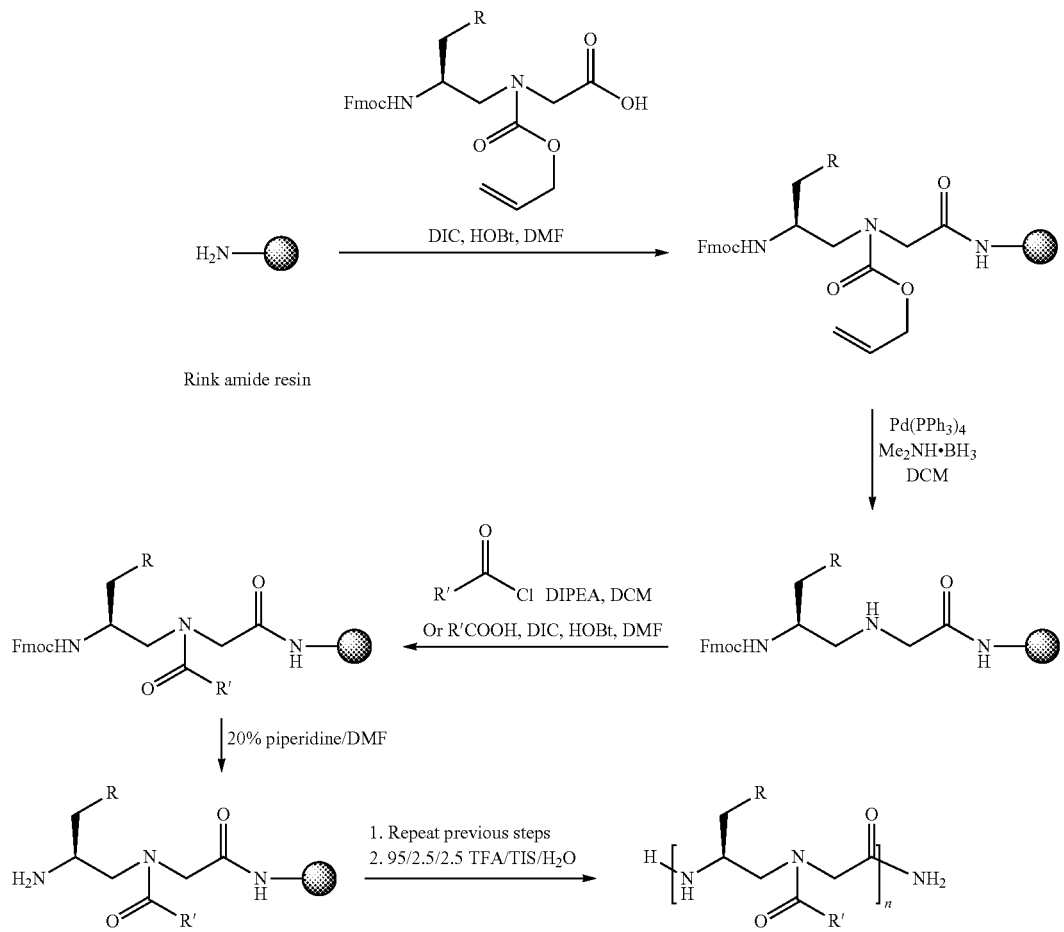

Scheme 2A (an embodiment of Scheme 2, Figure 3). Solid phase γ-AApeptide synthesis.

Solid phase synthesis was conducted on Rink amide resin (0.7 mmol/g) in peptide synthesis vessels on a Burrell Wrist-Action shaker (Scheme 2A). 100 mg resin (0.07 mmol) was treated with 3 mL 20% Piperidine/DMF solution for 15 min (×2) to remove Fmoc protecting group. The solution was drained and beads were washed with DCM (3×3 mL) and DMF (3×3 mL). A solution of γ-AApeptide building block (2 eqiv.), HOBt (38 mg, 0.28 mmol), and DIC (44 μL, 0.28 mmol) in 3 mL DMF was shaken for 5 min, and then added to the resin in a peptide synthesis vessel. The mixture was allowed to react at room temperature for 6 h and drained. The beads were washed with DCM (3×3 mL) and DMF (3×3 mL), followed by a capping reaction with 500 μL acetic anhydride in 3 mL Pyridine. After washing with DMF (3×3 mL) and DCM (3×3 mL), to the beads were added $Pd(PPh_3)_4$ (8 mg, 0.007 mmol) and $Me_2NH \cdot BH_3$ (25 mg, 0.42 mmol) in 3 mL DCM (Gomez-Martinez, P.; Dessolin, M.; Guibe, F.; Albericio, F. *J Chem Soc Perk T* 1 1999, 2871, hereby incorporated by reference herein for bead preparation). The alloc deprotection reaction was shaken for 10 min and repeated one more time. The beads were washed with DCM and DMF, followed by the reaction with acid chloride (4 eqiv.) and DIPEA (6 eqiv.) in 3 mL DCM for 30 min (×2) or with carboxylic acid (4 equiv.), HOBt (8 eqiv.), and DIC (8 eqiv.) for 4 h (×2).

The previous steps were repeated until the desired sequences were obtained. After that, the resin were washed with DCM and dried in vacuo. Peptide cleavage was done in a 4 mL vial by treating resin with $TFA/H_2O/TIS$ (95/2.5/2.5) for 2 h. The solvent was evaporated and the crude was analyzed and purified on an analytical (1 mL/min) and a preparative (20 mL/min) Waters HPLC systems, respectively. 5% to 100% linear gradient of solvent B (0.1% TFA in acetonitrile) in A (0.1% TFA in water) over 40 min was used. The HPLC traces were detected at 215 nm. The products were confirmed on an Applied Biosystems 4700 Proteomics Analyzer. Then, the desired fractions were collected and lyophilized.

Figure 6:
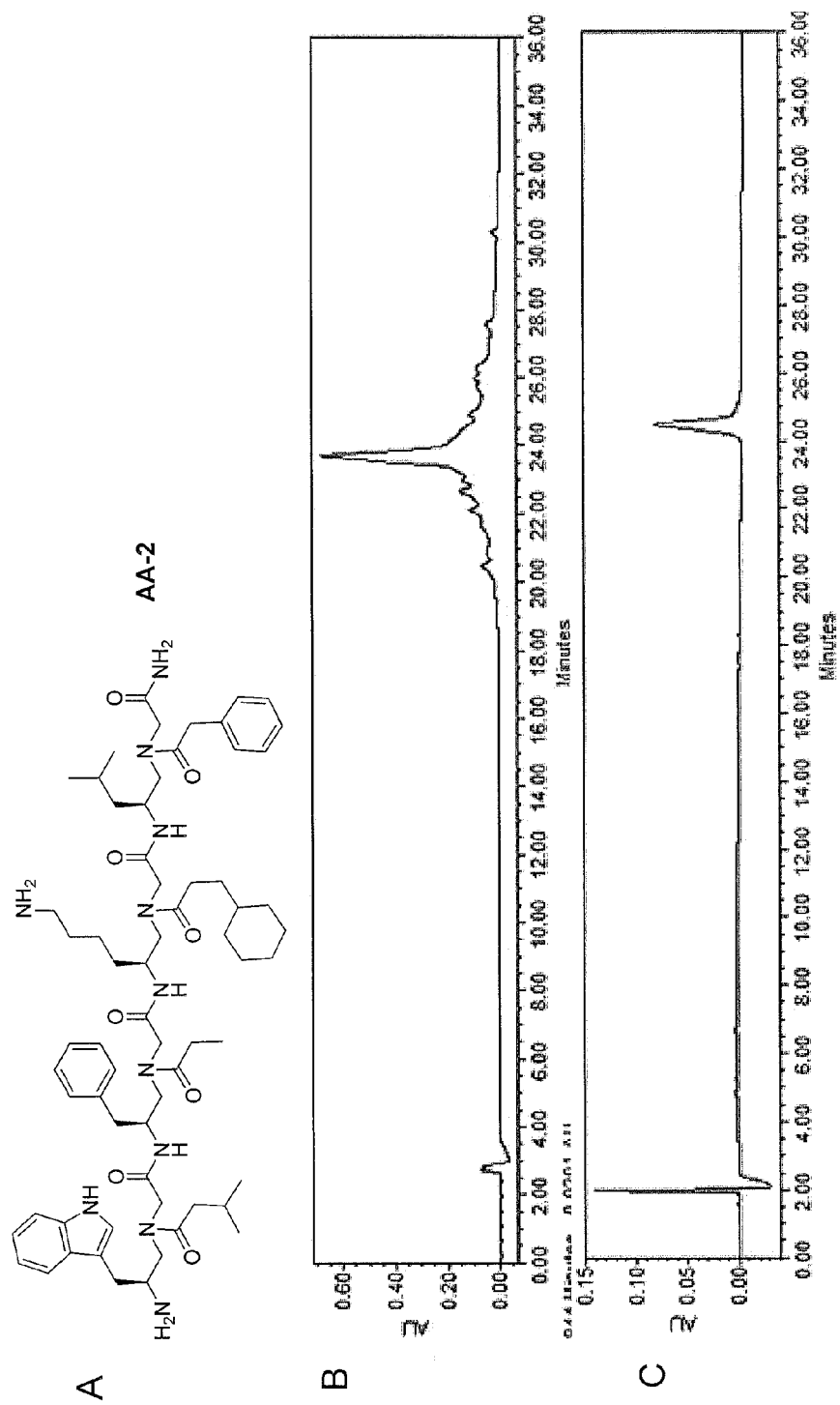
FIGS. 6A-6C illustrate the chemical structure of model compound AA-2 (FIG. 6A), the analytical HPLC trace for crude product (FIG. 6B), and the analytical HPLC trace for purified product (FIG. 6C).

The method was tested by synthesizing two model compounds: AA-1 and AA-2. Their crude and pure analytical traces are shown in FIGS. 5 and 6 and additional details are presented in Table 2, below.

TABLE 2

MALDI analysis of γ-AApeptides.

| γ-AApeptides | Purity (Based on crude HPLC trace) | Yield (based on loading of the resin) | Exact mass (Actual) | Exact mass (found) |
|---|---|---|---|---|
| AA-1 | 65% | 10.5% | 1817.0280 | 1818.0890 ($+H^+$) |
| AA-2 | >80% | 12% | 1159.7522 | 1160.8005 ($+H^+$) |

4. MS/MS Analysis

The fragmentation pattern of a known γ-AApeptide was analyzed on a Thermo Scientific LTQ Orbitrap XL mass spectrometer (FIG. 7). Higher Energy Collision Dissociation (HCD) was performed at collision energy of 35.

5. Synthesis of the OBOC γ-AApeptide Library

An embodiment of library synthesis as performed in the present example is illustrated in scheme 3 shown in FIG. 8. The TentaGel $NH_2$ resin (1.6 g, 0.48 mmol, 832,000 beads) was swelled in DMF for 1 h, followed by the treatment with Fmoc-Met-OH (3 eqiv.), HOBt (6 eqiv.), and DIC (6 eqiv.) in DMF (as described in Aquino, C.; Sarkar, M.; Chalmers, M. J.; Mendes, K.; Kodadek, T.; Micalizio, G. C. *Nat Chem* 2012, 4, 99, incorporated by reference herein for bead preparation and treatment). The beads were shaken at room temperature in a peptide synthesis vessel for 4 h and repeated. The beads were washed with DCM (×3) and DMF (×3). Fmoc protecting group was removed with 20% piperidine in DMF for 20 min (×2). The beads were washed and equally distributed into four peptide synthesis vessels.

Each building block (2 eqiv.) together with HOBt (4 eqiv.) and DIC (4 eqiv.) were dissolved in DMF and added to each vessel. The coupling reaction was performed at room temperature for 6 h and repeated. The beads in each vessel were then washed and mixed thoroughly by severe shaking for 1 h. The beads were equally split into five vessels. The Alloc protecting group was removed by treating beads with $Pd(PPh_3)_4$ (0.1 eqiv.) and $Me_2NH \cdot BH_3$ (6 eqiv.) in DCM for 10 min (×2). After washing, each portion was reacted with either acid chloride or carboxylic acid. The reaction with acid chloride (5 eqiv.) was carried out in the presence of DIPEA (5 eqiv.) and DCM for 30 min (×2). The carboxylic acids (3 eqiv.) were pre-activated with DIC (6 eqiv.) and HOBt (6 eqiv.) in DMF, then added to beads. The reaction was carried out by shaking the vessel for 6 hours and repeated.

After that, all the beads were pooled and mixed thoroughly. The previous split-and-pool process was repeated three times. The last time, after attachment of building blocks, beads were equally distributed into six portions, five of which were treated with alloc deprotection reagents then with acid chlorides and carboxylic acids as shown previously. The sixth portion was kept unreacted. At last, all beads were combined in one peptide synthesis vessel and washed thoroughly with DMF and DCM. Beads were treated with 20% piperidine in DMF for 20 min (×2) and then with $TFA/TIS/H_2O$ (95:2.5:2.5) for 2 h to remove all the protecting groups. The beads were washed with DCM thoroughly and dried in vacuo.

Figure 9:
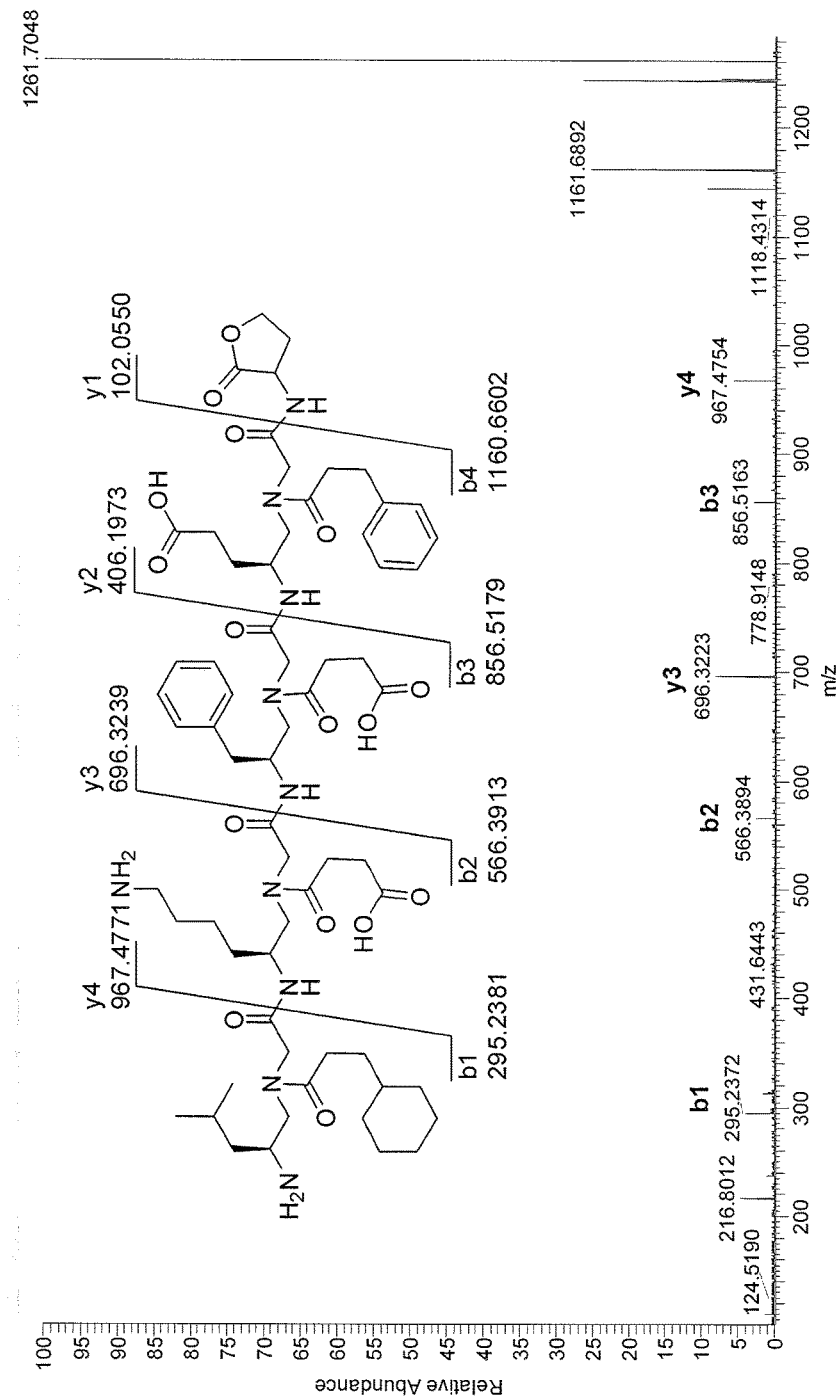
FIG. 9 illustrates the elucidated chemical structure and HCD fragmentation pattern of an unknown γ-AApeptide from a random bead. HCD fragmentation of a single charged precursor ion (1261.7095) was performed at collision energy of 25.

One random bead from the library was treated with 20 μL CNBr solution (50 mg in 1 mL 5:4:1 acetonitrile/acetic acid/water solution) (see Aquino, above, incorporated by reference). After overnight reaction, all the solvents and CNBr were removed using a Thermo Scientific Savant SPD131DDA SpeedVac system. The compound was re-dissolved in 30 μL water and applied on a Supelco Discovery DSC-18 SPE tube. The 50:50 acetonitrile/water elution was collected. HCD fragmentation of a double charged precursor ion was represented in FIG. 9. The structure of the unknown sequence was identified (FIG. 9).

Combinatorial Library Screening

1. General Information

The amyloid beta peptide $A\beta_{40}$ was used as a target for the combinatorial library screen because insoluble Aβ plaque was thought to be a pathological marker in Alzheimer's disease (AD). The synthesized library was stored in a peptide synthesis vessel, and later washed and incubated in the same container. The antibodies were purchased from Fisher Scientific, and all the other chemicals were provided by Sigma-Aldrich. The beads were screened and picked up under Zeiss inverted fluorescence microscope 10×43HE filter.

2. Beads Screening

The library synthesized on TentaGel beads was swelled in dimethylformamide (DMF) for 1 hour, washed with 1×TBST for five times and then equilibrated in 1×TBST overnight at room temperature, as described in Aquino (supra, incorporated by reference herein). The beads were blocked in 1% BSA in TBST for 1 hour, washed and equilibrated in 1×PBST before prescreening and screening.

Prescreening:

In order to avoid any possible nonspecific binding, both the Aβ and antibodies solution were made in 1% BSA/TBST blocking buffer. The library was first incubated with mouse 6e10 primary antibody which recognizes the first 16 amino acids of Aβ1-40, followed by five times PBST wash and incubation with goat anti-mouse IgG conjugated with dylight 549. The beads were washed with PBST completely and transferred into a 6-well plate to be observed under Zeiss inverted fluorescence microscope 10×43HE filter, and the orange bright beads were picked up for they had suspicious nonspecific binding.

The rest of the beads were pulled together, washed with PBST, and then treated with 1% SDS at 90° C. for ten minutes to remove any bound proteins. Water and TBST were used to wash away the SDS and then the beads were washed and swelled in DMF for 1 hour. After washing and equilibrating in TBST overnight, the beads were ready for actual Aβ screening.

Screening:

The prescreened beads were equilibrated in 1% BSA/PBST for 1 hour at room temperature. After washing with PBST for three times, the beads were incubated with Aβ$_{40}$ peptide at a concentration of 20 µg/mL for 4 hours at room temperature. After thorough washing with PBST, the library beads were incubated in 5 mL of 1% BSA/PBST containing 1:5000 diluted mouse 6e10 antibodies for 2 hours at room temperature. The beads were gently washed with PBST and incubated with 1:500 diluted goat anti-mouse IgG-dylight 549 for 1 hour at room temperature. The beads were washed with PBST and transferred into the 6-well plate to be observed under Zeiss inverted fluorescence microscope 10×43HE filter. Again the bright orange ones were picked up as candidates for further study.

3. Sequence Decoding

The beads were collected and washed with 1×PBST three times. The bound fluorescent dyes, proteins, and antibodies were removed by treating beads with 1% SDS solution at 90° C. for 10 min. Washed with water, DMSO, and acetonitrile, beads were then cleaved and analyzed using previous procedure. The structure of one hit was determined (FIG. 11) and designated as HW-155-1.

4. Solid Phase Synthesis of HW-155-1 and KLVFF Peptide

Figure 13:
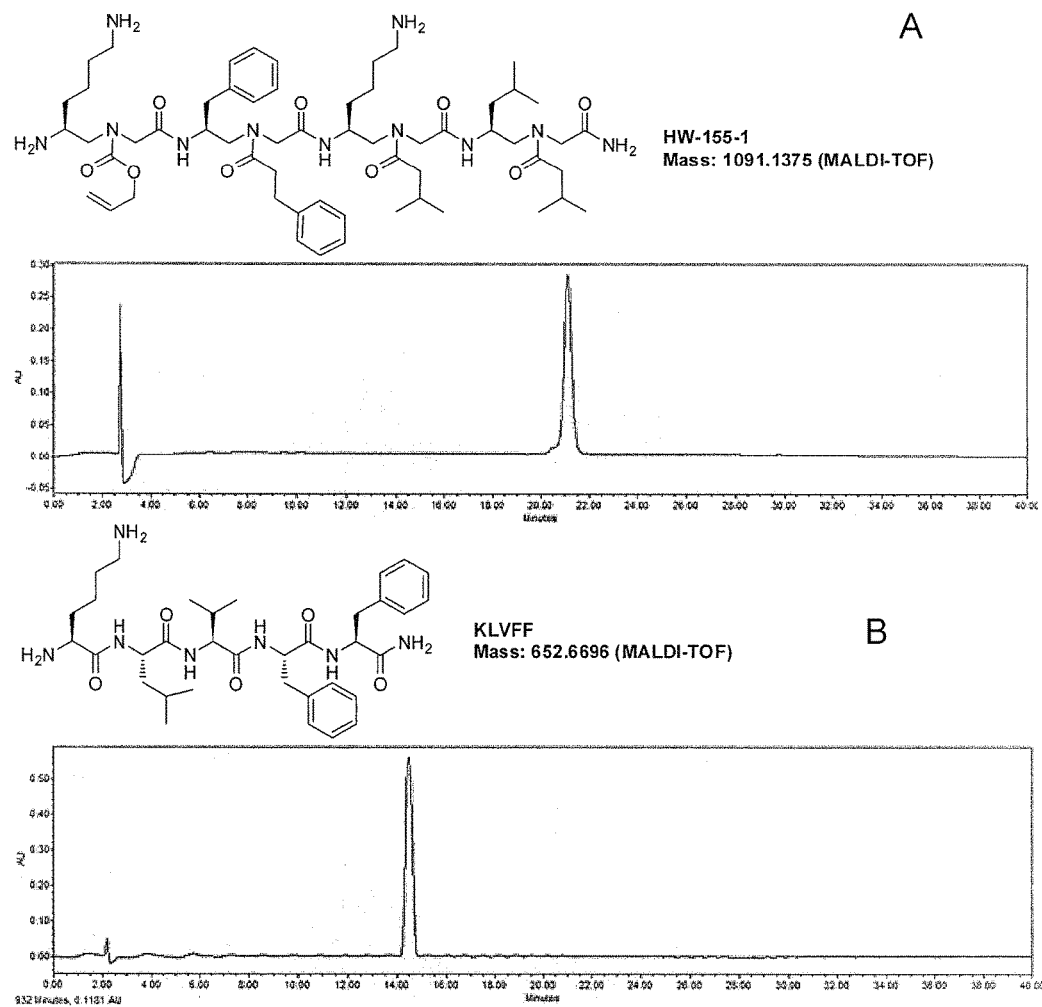
FIGS. 13A and 13B illustrate the chemical structures and pure HPLC traces of compound HW-155-1 (FIG. 13A) and KLVFF peptide (FIG. 13B).

HW-155-1 was resynthesized on rink amide resin following previous procedure. (Scheme 2A) The mass was determined to be 1091.1375 (M+H)$^+$ on an Applied Biosystems 4700 Proteomics Analyzer. The purity was analyzed on an analytical Waters HPLC system with flow rate of 0.8 mL/min and linear gradient from 5% to 100% (CH$_3$CN in water) in 40 min (FIG. 13A). As a positive control, KLVFF sequence was synthesized manually using regular solid phase peptide synthesis method. Amino acids were assembled on rink amide resin individually using HOBt/DIC as coupling reagents. After cleavage with TFA/TIS/H$_2$O (95:2.5:2.5) for 3 h, TFA was removed under reduced pressure. The peptide was purified and analyzed on a preparative and analytical Waters HPLC system, respectively. (FIG. 13B).

Functional Bioassays

1. Thioflavin T Assay

Compounds in different concentrations in Tris buffer Saline (TBS, pH 7.5) containing 10 µM ThT were added into a black 96 well plate corning@3721. Aβ$_{40}$ monomer was freshly thawed and used to make a stock solution in TBS with a concentration of 5 µM. Equal volume of Aβ solution was added into the 96 well palate (final Aβ concentration was 2.5 µM). Time-dependent fluorescence change was monitored by a Synergy 2 plate reader at an excitation wavelength of 440 nm and emission at 482 nm. After 24 h, the fluorescence change was recorded. 100% aggregation is the fluorescence change of 2.5 µM Aβ$_{40}$ in TBS buffer containing 5 µM ThT.

2. Transmission Electron Microscopy (TEM)

Aβ$_{40}$ preparations were adsorbed onto 200-mesh copper grids for 1 hour (until it is dry), and then stained with 1% uranyl acetate for 20 sec. The excess fluid was removed and the grids were analyzed with FEI Morgagni 268D TEM operated at 60 kV.

3. MTT Toxicity Assay

In siliconized tubes, Aβ$_{42}$ peptide of 10 µM (in F-12 medium) were pre-incubated with 0, 0.5 and 1 equiv. HW-155-1 AApeptide, respectively. These solutions were incubated on rotating shaker (Barnstead 400100) at 8 rpm in 37° C. for 24 h. Meanwhile, N2a cells were plated in 96-well plates (10000 cells/well) with triple replications for 24 h. Then pre-aggregated mixtures were added into each well to make the final Aβ concentration at 1 µM. The plate was incubated for another 24 h. Next, 10 µL MTT reagent was added to the cells. The plate was incubated for 4 h at 37° C. After the addition of 100 µL solubilization solution and incubation overnight, OD values were read at 575 nm. The final cell viability was calculated as:

Cell viability %=(OD575−OD blank)/(ODctrl−OD blank)×100%.

In regard to the discussion herein including the Examples above and the claims, it should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to measurement techniques and the units of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

REFERENCES

If indicated in the description above, the following references are incorporated by reference herein.

1. Kodadek, T. The rise, fall and reinvention of combinatorial chemistry. *Chemical Communications* 47, 9757-9763 (2011).
2. Aquino, C. et al. A biomimetic polyketide-inspired approach to small-molecule ligand discovery. *Nature chemistry* 4, 99-104 (2012).
3. Simpson, L. S. & Kodadek, T. A cleavable scaffold strategy for the synthesis of one-bead one-compound cyclic peptoid libraries that can be sequenced by tandem mass spectrometry. *Tetrahedron Letters* 53, 2341-2344 (2012).
4. Aditya, A. & Kodadek, T. Incorporation of Heterocycles into the Backbone of Peptoids to Generate Diverse Peptoid-Inspired One Bead One Compound Libraries. *Acs Comb Sci* 14, 164-169 (2012).
5. Udugamasooriya, D. G. & Kodadek, T. On-Bead Two-Color (OBTC) Cell Screen for Direct Identification of Highly Selective Cell Surface Receptor Ligands. *Current protocols in chemical biology* 4, 35-48 (2012).
6. Kodadek, T. Development of antibody surrogates for the treatment of cancers and autoimmune disease. *Current opinion in chemical biology* 14, 721-727 (2010).
7. Zuckermann, R. N. & Kodadek, T. Peptoids as potential therapeutics. *Curr Opin Mol Ther* 11, 299-307 (2009).
8. Astle, J. M. et al. Seamless bead to microarray screening: rapid identification of the highest affinity protein ligands from large combinatorial libraries. *Chemistry & biology* 17, 38-45 (2010).
9. Kodadek, T. Rethinking screening. *Nature chemical biology* 6, 162-165 (2010).
10. Lam, K. S. et al. A New Type of Synthetic Peptide Library for Identifying Ligand-Binding Activity. *Nature* 354, 82-84 (1991).
11. Lam, K. S. Editorial: Peptides as cancer therapeutics. *Biopolymers* 66, 141-141 (2002).
12. Aina, O. H., Sroka, T. C., Chen, M. L. & Lam, K. S. Therapeutic cancer targeting peptides. *Biopolymers* 66, 184-199 (2002).
13. Copeland, G. T. & Miller, S. J. Selection of enantioselective acyl transfer catalysts from a pooled peptide library through a fluorescence-based activity assay: An approach to kinetic resolution of secondary alcohols of broad structural scope. *Journal of the American Chemical Society* 123, 6496-6502 (2001).
14. Kritzer, J. A., Luedtke, N. W., Harker, E. A. & Schepartz, A. A rapid library screen for tailoring beta-peptide structure and function. *Journal of the American Chemical Society* 127, 14584-14585 (2005).
15. Hayashi, R. et al. N-acylpolyamine inhibitors of HDM2 and HDMX binding to p53. *Bioorganic & medicinal chemistry* 17, 7884-7893 (2009).
16. Iera, J. A., Jenkins, L. M. M., Kajiyama, H., Kopp, J. B. & Appella, D. H. Solid-phase synthesis and screening of N-acylated polyamine (NAPA) combinatorial libraries for protein binding. *Bioorganic & Medicinal Chemistry Letters* 20, 6500-6503 (2010).
17. Niu, Y. et al. Identification of gamma-AApeptides with potent and broad-spectrum antimicrobial activity. *Chemical communications* (Cambridge, England) 47, 12197-12199 (2011).
18. Niu, Y. et al. Cellular Translocation of a gamma-AApeptide Mimetic of Tat Peptide. *Molecular pharmaceutics*, 1529 (2012).
19. Niu, Y., Jones, A. J., Wu, H., Varani, G. & Cai, J. gamma-AApeptides bind to RNA by mimicking RNA-binding proteins. *Org Biomol Chem* 9, 6604-6609 (2011).
20. Niu, Y., Hu, Y., Li, X., Chen, J. & Cai, J. [gamma]-AApeptides: design, synthesis and evaluation. *New Journal of Chemistry* 35, 542-545 (2011).
21. Wu, H. et al. Solid-Phase Synthesis of gamma-AApeptides Using a Submonomeric Approach. *Organic letters* 14, 3446-3449 (2012).
22. Wu, H. et al. Design and synthesis of unprecedented cyclic gamma-AApeptides for antimicrobial development. *Chem. Sci.* 3 2570-2575 (2012).
23. Niu, Y. et al. Lipo-gamma-AApeptides as a New Class of Potent and Broad-Spectrum Antimicrobial Agents. *Journal of medicinal chemistry* 55, 4003-4009 (2012).
24. Niu, Y. et al. Nanorods Formed from a New Class of Peptidomimetics. *Macromolecules* 45, 7350 (2012).
25. Rapireddy, S., He, G., Roy, S., Armitage, B. A. & Ly, D. H. Strand invasion of mixed-sequence B-DNA by acridine-linked, gamma-peptide nucleic acid (gamma-PNA). *Journal of the American Chemical Society* 129, 15596-15600 (2007).
26. Yang, Y. A. et al. Radiolabeled gamma-AApeptides: a new class of tracers for positron emission tomography. *Chemical Communications* 48, 7850-7852 (2012).
27. Gomez-Martinez, P., Dessolin, M., Guibe, F. & Albericio, F. N-alpha-Alloc temporary protection in solid-phase peptide synthesis. The use of amine-borane complexes as allyl group scavengers. *Journal of the Chemical Society-Perkin Transactions* 1, 2871-2874 (1999).
28. Upadhaya, A. R., Lungrin, I., Yamaguchi, H., Fandrich, M. & Thal, D. R. High-molecular weight Aβ-oligomers and protofibrils are the predominant Aβ-species in the native soluble protein fraction of the AD brain. *Journal of Cellular and Molecular Medicine*, no-no (2011).
29. Bernstein, S. L. et al. Amyloid beta-protein: monomer structure and early aggregation states of Abeta42 and its Pro19 alloform. *Journal of the American Chemical Society* 127, 2075-2084 (2005).
30. Jakob-Roetne, R. & Jacobsen, H. Alzheimer's Disease: From Pathology to Therapeutic Approaches. *Angewandte Chemie-International Edition* 48, 3030-3059 (2009).
31. Luo, Y. et al. Abeta42-Binding Peptides as Amyloid Aggregation Inhibitors and Detection Ligands. *ACS Chemical Neuroscience* 4, 952 (2013).
32. Chafekar, S. M. et al. Branched KLVFF tetramers strongly potentiate inhibition of beta-amyloid aggregation. *Chembiochem* 8, 1857-1864 (2007).
33. Cheng, P. N., Spencer, R., Woods, R. J., Glabe, C. G. & Nowick, J. S. Heterodivalent Linked Macrocyclic beta-Sheets with Enhanced Activity against A beta Aggregation: Two Sites Are Better Than One. *Journal of the American Chemical Society* 134, 14179-14184 (2012).
34. Cheng, P. N., Liu, C., Zhao, M. L., Eisenberg, D. & Nowick, J. S. Amyloid beta-sheet mimics that antagonize protein aggregation and reduce amyloid toxicity. *Nature chemistry* 4, 927-933 (2012).
35. Cheng, P. N. & Nowick, J. S. Mimicry of amyloid b-sheets. *Abstracts of Papers of the American Chemical Society* 240(2010).
36. Soto, C. et al. Beta-sheet breaker peptides inhibit fibrillogenesis in a rat brain model of amyloidosis: implications for Alzheimer's therapy. *Nature medicine* 4, 822-826 (1998).
37. Zhang, G. B., Leibowitz, M. J., Sinko, P. J. & Stein, S. Multiple-peptide conjugates for binding beta-amyloid plaques of Alzheimer's disease. *Bioconjugate chemistry* 14, 86-92 (2003).
38. Rahimi, F., Murakami, K., Summers, J. L., Chen, C. H. B. & Bitan, G. RNA Aptamers Generated against Oligomeric A beta 40 Recognize Common Amyloid Aptatopes with Low Specificity but High Sensitivity. *PloS one* 4(2009).
39. Ylera, F., Lurz, R., Erdmann, V. A. & Furste, J. P. Selection of RNA aptamers to the Alzheimer's disease amyloid peptide. *Biochem Bioph Res Co* 290, 1583-1588 (2002).
40. Pauwels, K. et al. Structural Basis for Increased Toxicity of Pathological A beta(42):A beta(40) Ratios in Alzheimer Disease. *Journal of Biological Chemistry* 287, 5650-5660 (2012).
41. Hooper, C.; Killick, R.; Lovestone, S. *J Neurochem* 2008, 104, 1433.

We claim:

1. A method of making a γ-AApeptide library, the method comprising:
   a. providing a plurality of synthetic beads functionalized to react with γ-AApeptide building blocks;
   b. splitting the beads into a predetermined number of groups and placing each group in a separate reaction vessel;
   c. adding a different γ-AApeptide building block to each reaction vessel and reacting the γ-AApeptide building block with the beads, wherein each γ-AApeptide building block has the structure of compound X

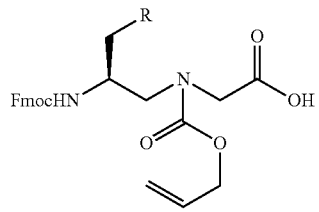

compound X and wherein the R for the γ-AApeptide building block for each reaction vessel is different from that for every other reaction vessel and is selected from the group consisting of: any amino acid side chain;
   d. pooling the bead/γ-AApeptide compounds from each reaction vessel together, then splitting the pooled bead/γ-AApeptide compounds into the predetermined number of groups, and placing each group into a separate reaction vessel;
   e. removing the alloc protection groups from the bead/γ-AApeptide compounds;
   f. adding a different acylating agent to each reaction vessel, wherein each acylating agent includes an R' group, and wherein the R' for each different acylating agent is independently selected from the group consisting of: any amino acid side chain,

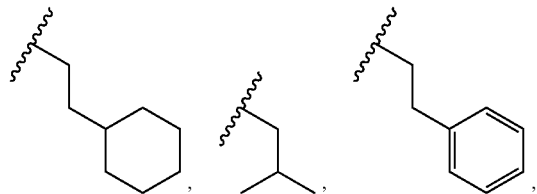

-continued

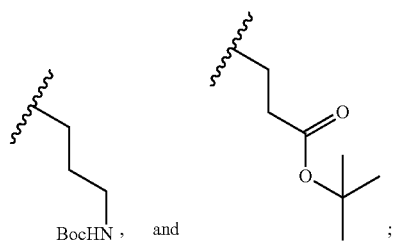

BocHN, and ;

g. pooling the bead/acylated γ-AApeptide compounds from each reaction vessel together, then splitting the pooled bead/acylated γ-AApeptide compounds into the predetermined number of groups, and placing each group into the separate reaction vessels;
   h. repeating steps c-g n−1 number of times; and
   i. removing all protecting groups to obtain a library of different γ-AApeptide compounds having a structure of Formula I:

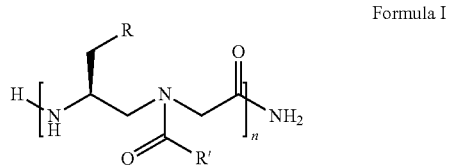

Formula I wherein, for each γ-AApeptide compound, n is an integer between 1 and about 20, the bracketed portion of Formula I is a repeating unit, except for the identity of R and R', and R and R' are as defined above and are independently selected for each repeating unit.

2. The method of claim 1 wherein each acylating agent is selected from a carboxylic acid and an acid chloride.

3. A method of screening a library of γ-AApeptides for ligands to a target compound, the method comprising:
   j. contacting the γ-AApeptides in the library with a target compound, each γ-AApeptide in the library having a structure of Formula I:

Formula I

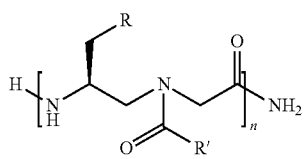

wherein, for each γ-AApeptide compound, n is an integer between 1 and about 20, the bracketed portion of Formula I is a repeating unit, except for the identity of R and R', and R and R' are independently selected for each repeating unit, wherein R is independently selected from any amino acid side chain and R' is independently selected from the group consisting of any amino acid side chain,

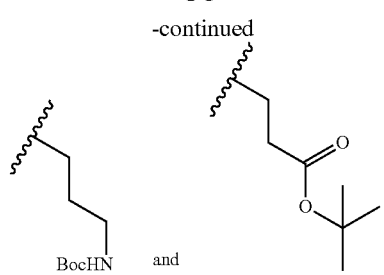

removing unbound target compound;
contacting the library with an antibody capable of binding the target compound;
detecting the antibody with a compound capable of producing a detectable signal; and
selecting the γ-AApeptide associated with the detectable signal, wherein the selected γ-AApeptide is a ligand capable of binding the target compound.

4. The method of claim 3, wherein the compound capable of producing the detectable signal comprises a second antibody capable of binding the first antibody, wherein the second antibody comprises a detectable label.

5. The method of claim 3 wherein the detectable label is selected from the group of detectable labels consisting of: a fluorescent molecule, a magnetic molecule, and a radiolabel.

6. The method of claim 3, wherein the target is an Aβ peptide.

7. The method of claim 6, wherein the Aβ peptide is Aβ$_{40}$, Aβ$_{42}$, or both.

8. A γ-AApeptide having the following structure:

Compound HW-155-1

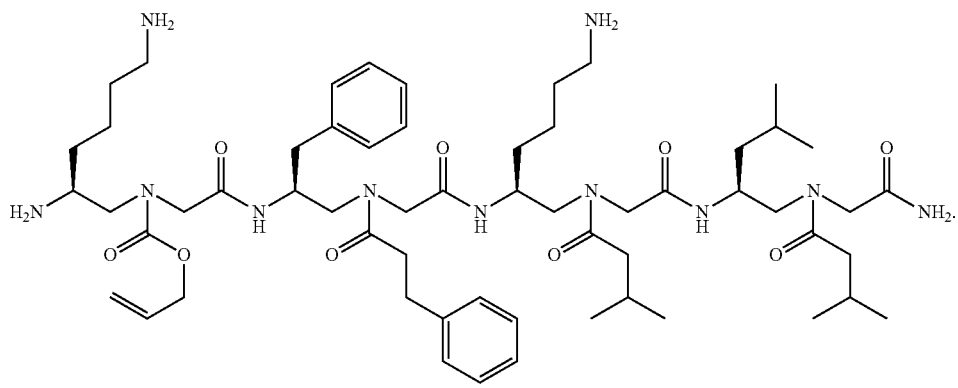

9. The method of claim 6, wherein the selected γ-AApeptide is capable of inhibiting aggregation of Aβ peptides.

10. The method of claim 9, wherein the Aβ peptide is Aβ$_{40}$, Aβ$_{42}$, or both.

11. The method of claim 9, wherein inhibition of aggregation of Aβ peptides inhibits formation of Aβ fibrils.

12. The method of claim 9, wherein the inhibition of aggregation of Aβ peptides is performed in vivo or in vitro.

13. The compound of claim 8, further comprising:
a detectible label coupled to γ-AApeptide HW-155-1.

* * * * *